United States Patent

Hozumi et al.

[11] Patent Number: 5,411,733
[45] Date of Patent: May 2, 1995

[54] ANTIVIRAL AGENT CONTAINING CRUDE DRUG

[76] Inventors: Toyoharu Hozumi, 30-9, Toyotamakita 5-chome, Nerima-ku, Tokyo; Takao Matsumoto, 1-31, Kamiimaizumi 6-chome, Ebina-shi, Kanagawa; Haruo Ooyama, 89-203, Tsurugamine 1-chome, Asahi-ku, Yokohama-shi, Kanagawa; Tsuneo Namba, 1-104, 2556-4, Gofukusehiro-cho, Toyama-shi, Toyama; Kimiyasu Shiraki, 2-202, 2556-4, Gofukusuehiro-cho, Toyama-shi, Toyama; Masao Hattori, 2-203, 2556-4, Gofukusuehiro-cho, Toyama-shi, Toyama; Masahiko Kurokawa, 2-101, 2-2, Minamitaikouyama, Kosugi-machi, Imizu-gun, Toyama; Shigetoshi Kadota, 2-402, 2556-4, Gofukusuehiro-cho, Toyama-shi, Toyama, all of Japan

[21] Appl. No.: 51,647

[22] Filed: Apr. 26, 1993

[30] Foreign Application Priority Data

Apr. 27, 1992 [JP] Japan .................... 4-107659
Apr. 27, 1992 [JP] Japan .................... 4-107672

[51] Int. Cl.⁶ .................................... A61K 35/78
[52] U.S. Cl. ........................ 424/195.1; 514/520; 514/934
[58] Field of Search ............... 424/195.1; 514/520, 514/934

[56] References Cited

U.S. PATENT DOCUMENTS

| 4,442,087 | 4/1984 | Kojima et al. ............... 424/85 |
| 4,592,910 | 6/1986 | Wolf et al. .............. 424/195.1 |
| 4,595,593 | 6/1986 | Wolf et al. .............. 424/195.1 |
| 4,871,540 | 10/1989 | Kojima et al. ........... 424/195.1 |

FOREIGN PATENT DOCUMENTS

| 0003318 | 8/1979 | European Pat. Off. ...... A61K 35/78 |
| 0045718 | 2/1982 | European Pat. Off. ...... A61K 9/06 |
| 2442633 | 6/1980 | France ................. A61K 35/78 |
| 2446110 | 8/1980 | France ................. A61K 37/02 |
| 2078753 | 1/1982 | United Kingdom ........ A61K 35/78 |
| 8805304 | 7/1988 | WIPO ................... A61K 35/78 |

OTHER PUBLICATIONS

Ito et al., Antiviral Research, 7, 127–137 (1987).
Hudson, Antiviral Research, 12, 55–74 (1989).
Field et al., Antiviral Research, 2, 243–254 (1982).
The Lancet, Mar. 28, 1981, 705–706 "Viruses and Duodenal Ulcer".
Sydiskis et al. Antimircrobial Agents and Chemotherapy, 35(12), 2463–2466 (1991).
Yamamoto et al., Antiviral Research 12, 21–36 (1989).
Tang et al., Antiviral Research, 13, 313–325 (1990).
Fukuchi et al., Antiviral Research, 11, 285–297 (1989).
Amoros et al., Antiviral Research, 8, 13–25 (1987).
Shiraki, Intervirology, 29, 235–240 (1988).
Takechi et al., Planta Medica, 42, 69–74 (1981).
Nagai et al., Biochemical and Biophysical Research Communications, 163(1), 25–31 (1989).
Ono et al., Biomed & Pharmacother, 44, 13–16 (1990).
Nagai et al., Chem. Pharm. Bull. 38(5), 1329–1332 (1990).
Kane et al., Bioscience Reports, 8(1), 85–94 (1988).
Ito et al., Antiviral Research, 7, 127–137 (1987).
Kumano et al., Antiviral Research, 7, 289–301 (1987).
Arai et al., J. of Medical and Pharmaceutical Society for WAKAN-YAKU, 4, 402–403 (1987).
Bohlmann, Ferdinand et al., 'Guaianolides from Ainsliaea Fragrans' *abstract* & Phytochemistry, Biological Abstracts, vol. 75, 1983, Phila., Pa., US; Abstract No. 36076.

(List continued on next page.)

*Primary Examiner*—John W. Rollins
*Attorney, Agent, or Firm*—Sughrue, Mion, Zinn, Macpeak & Seas

[57] ABSTRACT

Antiviral agent containing a crude drug effective on a broad range of viruses.

5 Claims, No Drawings

OTHER PUBLICATIONS

Database WPI, Week 9115, Derwent Publications Ltd., London, GB; AN 91-104775 & JP-A-3 041 030 (Sasaki H) 21 Feb. 1991 *abstract*.

Database WPI, Week 9013, Derwent Publications Ltd., London, GB; AN 90-094587 & JP-A-045 499 (Wakunaga Seiyaku KK) 15 Feb. 1990 *abstract*.

Database WPI, Week 9210, Derwent Publications Ltd., London, GB; AN 92-075194 & JP-A-4 018 019 (Kitasato Res Inst et al.) 22 Jan. 1992 *abstract*.

Database WPI, Week 9206, Derwent Publications Ltd., London, GB; AN 92-044315 & JP-A-3 287 526 (Daicel Chem Ind KK) 18 Dec. 1991 *abstract*.

Database WPI, Week 8731, Derwent Publications Ltd., London, GB; AN 87-216880 & JP-A-62 142 181 (Nihon Seifun KK) 25 Jun. 1987 *abstract*.

Database WPI, Week 9037, Derwent Publications Ltd., London, GB; AN 90-279258 & JP-A-2 196 725 (Nihon Seifun KK) 3 Aug. 1990 *abstract*.

Chemical Abstracts, vol. 95, No. 8, 1981, Columbus, Ohio, US; abstract No. 67850g, Takechi M. et al. 'Purification and Characterization of the Antiviral Substance from the Bud of Syzygium Aromatica' *abstract* & J Tradit Chin Med vol. 8, No. 3, 1988, pp. 203-206.

Biological Abstract, xol. 87, No. 2, 1989, Phila., Pa., US; abstract No. 14022, Zheng, Minshi 'An Experimental Study Of Antiviral Action Of 472 Herbs On Herpes Simplex Virus' *abstract* & J. Tradit Chin Med vol. 8, No. 3, 1988, pp. 203-206.

Database WPI, Week 9223, Derwent Publications Ltd., London, GB; AN 92-190105 & JP-A-4 128 237 (Nisshin Flour Milling Co) 28 Apr. 1992 *abstract*.

Database WPI, Week 9313, Derwent Publications Ltd., London, GB; AN 93-104206 & JP-A-5 043 477 (Nippon Mining Co et al.) 23 Feb. 1993 *abstract*.

ANTIVIRAL AGENT CONTAINING CRUDE DRUG

FIELD OF THE INVENTION

The present invention relates to an antiviral agent containing a crude drug.

BACKGROUND OF THE INVENTION

In recent years, opportunistic infectious diseases caused by viruses, such as cytomegalovirus (hereinafter abbreviated as CMV), in patients maintained on immunosuppressants, such as recipients of organ transplantation, have given rise to a problem. For instance, such infectious diseases have arisen the problem in the first living liver transplantation conducted in Shimane Medical Collage, Japan.

It has been clinically observed that the incidence of CMV infectious diseases varies depending on the combination of immunosuppressants administered to post-transplantation patients. Based on this observation, the present inventors studied the influences of individual immunosuppressants and combinations thereof on proliferation of CMV through in vitro testing systems. As a result, of various known immunosuppressants, cyclosporine and predonine accelerated CMV proliferation, while mizoribine and azathioprine inhibited CMV proliferation. These results are in good agreement with case reports as described below. Therefore, it is believed that substances exhibiting antiviral activity in vitro also possess antiviral activity in vivo.

More specifically, the cases have been reported in which CMV infection developed in 100% of patients on cyclosporine+predonine therapy whereas the incidence off CMV infection was as low as 51.5% or 63.6% in patients on the therapy with cyclosporine+predonine in combination with mizoribine or azathioprine, respectively, suggesting the contribution of mizoribine or azathioprine to the anti-CMV effect (see Shiraki K., et al., rinsho to virus, Vol. 18, pp. 25-29, "men-ekifuzenjotai ni okeru virus no saikasseika (Reactivation of virus in immunodeficiency)" (1990); Shiraki K., et al., Biomedica., vol. 5, pp. 65-69, "men-eki yokuseizai to CMV (Immunosuppressants and CMV)" (1990); Shiraki K., et al., Transplant. Proc., Vol. 22, pp. 1682-1685, "Effect of cyclosporine, azathioprine, mizoribine and predonine on replication of human cytomegalovirus" (1990); and Shiraki K., et al., Arch. Virol., Vol. 117, pp. 165-171, "Immunosuppressive dose of azathioprine inhibits replication of human cytomegalovirus" (1991).

The like observation applies to FK 506 and cyclosporine as immunosuppressants. It has been reported that FK 506 has no or slight inhibitory influence on CMV growth (see Shiraki K., et al., J. Antibiotics, Vol. 44, pp. 909-911, "Effect of FK 506 replication of human cytomegalovirus in vitro" (1991)), while cyclosporine reveals the above-mentioned results.

According to the clinical report of Alessiani, et al., no difference was recognized in the incidence of bacterial and fungal infectious diseases between liver transplantation recipients on FK 506+predonine therapy and those on cyclosporine+predonine therapy, while symptomatic CMV infectious disease developed in 0 out of 20 post-transplantation patients on the former therapy and 5 out of 20 post-transplantation patients on the latter therapy (see Alessiani M., et al., Transplant. Proc., Vol. 22, pp. 44-46, "Infection with FK 506 Immunosuppression; Preliminary results with primary therapy" (1990)). These clinical reports back up the CMV proliferation accelerating effect of cyclosporine observed in vitro.

Further, Bia, et al. made a case report that the incidence of CMV infection in post-transplantation patients on azathioprine+steroid therapy was about half that in those on cyclosporine+steroid therapy, and no severe case was observed in the former, both groups of patients having received no anti-T cell globulin (see Bia M. J., et al., Transplantation, Vol. 40, pp. 610-614, "Effect of treatment with cyclosporine versus azathioprine on incidence and severity of cytomegalovirus infection post-transplantation" (1985)).

Development of CMV infection is largely influenced by the immune condition of the host, the degree of immune suppression, and the like and does not seem to be decided simply by the combination of immunosuppressants. Nevertheless, it is understood that the clinical observations of post-transplantation patients account for the influences of immunosuppressants on CMV proliferation in vitro more duly than expected.

The above situation implies possibility to alleviate CMV infectious disease by use of some of drugs currently employed as immunosuppressants which exhibit mild, while not potent, antiviral activity.

The reason why immunosuppressants essentially having weaker anti-CMV activity than general antiviral agents eventually exhibit effective anti-CMV activity will be explained below. Taking CMV-caused pneumonia for instance, it takes about 2 weeks for the very early stage (in which the X-ray picture of the chest demonstrates changes which retrospectively appear abnormal) to develop into the stage which is clinically recognized as CMV penumonia. Tentatively setting the doubling time of CMV in the body at 72 hours (3 days), CMV increases 4 to 5 times within 2 weeks. Assuming that mizoribine or azathioprine controls CMV proliferation to half as described above, the amount of the virus will be controlled by administering mizoribine or azathioprine to one-thirty second through the 5-fold doubling period, i.e., about 3% of the amount of the virus in the case of using no mizoribine or azathioprine. It is considered natural that no CMV-caused disease occurs with such a small amount of CMV in patients on mizoribine or azathioprine therapy.

On the other hand, FK 506 hardly affects CMV proliferation, while cyclosporine accelerates CMV proliferation about twice. Accordingly, the CMV amount in the case of cyclosporine therapy will be 32 times that in the case of FK 506 therapy as calculated in the same manner as above. In addition, FK 506 is concentrated in the lung, the target organ of CMV infection, and the CMV proliferation is suppressed at that concentration by FK 506. This fact appears to contribute to the difference between FK 506 therapy and cyclosporine therapy.

Thus, it has now been revealed that use of an immunosuppressant having weak but effective anti-CMV activity possibly alleviates CMV infectious disease. Conventional studies have never been directed to the relationship between CMV and immunosuppressants from this point of view.

On the other hand, traditional medicines (such as traditional Chinese medicines and traditional Japanese medicines) (it is called crude drugs hereinafter) have been used for therapy for a long number of years, and ample knowledge of their usage, dosage, etc. has been accumulated. Many of crude drugs have minor or substantially no side effects. However, studies on antiviral activity of crude drugs are rare. The literature on this subject now available includes Ito M., et al., *Antiviral Research*, Vol. 7, pp. 127–137, "Inhibitory effect of glycyrrhizin on the in vitro infectivity and cytopathic activity of the human immunodeficiency virus [HIV (HTLV-III/LAV)]", (1987); Takechi M. and Tanaka Y., *Planta Medica*, Vol. 42, pp. 69–74, "Purification and characterization of antiviral substance from the bud of *Syzygium aromaticum*", (1981); Kane C. J. M., et al., *Bioscience Reports*, Vol. 8, pp. 85–94, "Methyl gallate, methyl-3,4,5-trihydroxybenzoate, is a potent and highly specific inhibitor of herpes simplex virus in vitro: I. Purification and characterization of methyl gallate from *Sapium sebiferum*", (1988); Nagai T., et al., *Chem. Pharm. Bull.*, Vol. 38, pp. 1329–1332, "Inhibition of influenza virus sialidase and anti-influenza virus activity by plant flavonoids", (1990); and Arai Y., et al., *J. of Medical and Pharmaceutical Society for WAKAN-YAKU*, Vol. 4, pp. 402–403, "Effect of *Bezoar bovis* against Chikungunya virus", (1987).

SUMMARY OF THE INVENTION

An object of the present invention is to provide an antiviral agent containing a crude drug having effectiveness on viral diseases, taking the above-mentioned relationship between CMV and immunosuppressants as persuasive and theoretical grounds for usefulness of some crude drugs which possess even non-potent but mild antiviral activity in the treatment of virus-caused diseases.

Another object of the present invention is to provide an antiviral agent containing a crude drug effective on a broad range of viruses.

The present inventors have conducted extensive investigations on a variety of crude drugs, including traditional Chinese medicines, Japanese medicines, and Indonesian medicines, which have conventionally been used as medicines, usage or dosage of which is known, and which involve no or a little side effect. As a result, they have found among them crude drugs having antiviral activity and thus reached the present invention.

The present invention relates to an antiviral agent containing at least one crude drug selected from the group consisting of (A1) the whole plant of *Ainsliaea fragrans* Champ., (A2) the rhizome of *Alpinia officinarum* Hance, (A3) the bark of *Alyxia stellata* Roem., (A4) the bark of *Andrographis paniculate* Nees, (A5) the root of *Andropogon zizaniodes* (L.) Urban, (A6) the rhizone of *Anemarrhena asphodeloides* Bunge, (A7) the leaf of *Arctostaphylos uva-ursi* (L.) Sprengel, (A8) the seed of *Areca catechu* L., (A9) the leaf of *Artemisia princeps* Pamp., (A10) the whole plant of *Asiasarum heterotropoides* F. Maekawa var. mandshuricum F. Maekawa, (A11) the rhizone of *Belamcanda chinensis* (L.) DC., (A12) the rhizome of *Brainia insignis* (Hook.) J. Sm., (A13) the seed of *Brucea javanica* (L.) Merr., (A14) the root of *Bupleurum fakatum* L., (A15) the bark of *Caesalpinia sappan* L., (A16) the leaf of *Camellia japonica* L., (A17) the bark of *Cassia fistula* L., (A18) the whole plant of *Chamaesyce hyssopifolia*, (A19) the bark and branch of *Cinnamomum cassia* Blume, (A20) the bark of *Cinnamomum sintok* Blume, (A21) the rhizome of *Cnidium officinale* Makino, (A22) the rhizome of *Coptis chinensis* Franch., (A23) the leaf of *Cordia spinescens*, (A24) the fruit of *Cornus officinalis* Sieb. et Zucc., (A25) the tuber of *Corvdalis hurtscharinorii* Besser forma yanhusuo Y. H. Chou et C. C. Hsu, (A26) the fruit of *Curculigo orchioides* Gaertn., (A27) the rhizome of *Curcuma aeroginosa* Roxb., (A28) the rhizome of *Curcuma xanthorrhiza* Roxb., (A29) the rhizome of *Cyrtomium fortunei* J. Sm., (A30) the rhizome of *Drynaria fortunei* (Kunze) J. Smith, (A31) the rhizome of *Dryopteris crassirhizoma* Nakai, (A32) the fruit of *Elaeocarpus grandiflorus* Smith, (A33) the leaf of *Elephantopus scaber* L., (A34) the leaf of *Epimedium koreanum* Nakai, (A35) the leaf of *Erythroxylum lucidum*, (A35') the trunk of *Erythroxylum citrifolium*, (A36) the fruit of *Evodia rutaecarpa* Hook. f. et Thoms., (A37) the fruit of *Foeniculum vulgare* Mill, (A38) the fruit of *Forsythia suspensa* Vahl., (A39) the whole plant of *Geranium thunbergii* Sieb. et Zucc., (A40) the whole plant of *Geum japonicum* Thung., (A41) the root and stolon of *Glycyrrhiza uralensis* Fisher (A42) the leaf of *Hamelia axillaris* Swartz, (A43) the branch and leaf of *Jatropha curcas* L., (A44) the bark of *Juglans mandshurica* Maxim., (A45) the root of *Lithospermum erythrorhizon* Sieb. et Zucc., (A46) the aerial part of *Loranthus parasiticus* (L.) Merr., (A47) the bark of *Machilus thunbergii* Sieb. et Zucc., (A48) the bark of *Magnolia officinalis* Rehd. et Wils., (A49) the rhizome of *Matteuccia struthiopteris* (L.) Todaro, (A50) the whole insect of *Mylabris sidae* Fabr., (A51) the root bark of *Paeonia suffruticosa* Andrews, (A52) the root of *Panax ginseng* C. A. Meyer, (A53) the bark of *Parameria laevigata* Moldenke, (A54) the leaf of *Perilla frutescens* Britton var. acuta Kudo, (A55) the bark of *Phellodendron amurense* Ruprecht, (A56) the aerial part of *Physalis anqulata* L., (A57) the rhizome of *Plagiogyria matsumureana* Makino, (A58) the root of *Platycodon grandiflorum* (Jacquin) A. DC., (A59) the root of *Polygala tenuifolia* Willd., (A60) the root and rhizome of *Polygonum cuspidatum* Sieb. et Zucc., (A61) the hoelen of *Poria cocos* Wolf, (A62) the spike of *Prunella vulgaris* L. subsp. asiatica Hara, (A63) the bark of *Prunus jamasakura* Siebold, (A64) the fruit of *Prunus mume* Sieb. et Zucc., (A65) the root bark and fruit peel of *Punica granatum* L., (A66) the bark of *Quercus acutissima* Carruthers, (A67) the leaf of *Quercus salicina* Blume, (A68) the fruit of *Quisqualis indica* L., (A69) the rhizome of *Rheum palmatum* L., (A70) the gall of *Rhus javanica* L., (A71) the root of *Salvia miltiorrhiza* Bunge, (A72) the leaf of *Sarcandra glabra* (Thunb.) Nakai, (A73) the flores of *Schizonepeta tenuifolia* Briquet, (A74) the root of *Scutellaria baicalensis* Georgi, (A75) the whole plant of *Serjania mexicana*, (A76) the flower bud of *Sophora japonica* L., (A77) the root of *Sophora subprostrata* Chun et T. Chen, (A78) the stem of *Spatholobus suberectus* Dunn, (A79) the rhizome of *Struthiopteris niponica* (Kunze) Nakai, (A80) the seed of *Strychnos nux-vomica* L., (A81) the flower bud of *SyzygiUm aromaticum* (L.) Merr. et Perry, (A82) the bark of *Terminalia arjuna* Wight et Arn., (A83) the fruit peel of *Terminalia belerica* Roxb., (A84) the fruit of *Terminalia chebula* Retzus, (A85) the leaf and branch of *Uncaria gambir* Roxb., (A86) the whole plant of *Usnea misaminensis* Vain., (A87) the branch and leaf of *Waltheria indica* L., (A88) the flower and leaf of *Woodfordia floribunda* Salisb., (A89) the rhizome of *Woodwardia orientalis* Sw., (A90) the fruit peel of *Zanthoxylum bungeanum* Maxim., and (A91) the fruit of *Zizyphus jujuba* Miller var. inermis Rehder (hereinafter referred to as group A).

The first embodiment of the present invention relates to an antiherpesviral agent containing at least one crude drug selected from the group consisting of (B1) the whole plant of *Ainsliaea fragrans* Champ., (B2) the rhizome of *Alpinia officinarum* Hance, (B3) the bark of *Alyxia stellata* Roem., (B4) the root of *Andropogon zizaniodes* (L.) Urban, (B5) the seed of *Areca catechu* L., (B6) the leaf of *Artemisia princeps* Pamp., (B7) the rhizome of *Brainia insignis* (Hook.) J. Sm., (B8) the seed of *Brucea javanica* (L.) Merr., (B9) the bark of *Caesalpinia sappan* L., (B10) the leaf of *Camellia japonica* L., (B11) the bark of *Cassia fistula* L., (B12) the whole plant of *Chamaesyce hyssopifolia*, (B13) the bark and branch of *Cinnamomum cassia* Blume, (B14) the bark of *Cinnamomum sintok* Blume, (B15) the rhizome of *Coptis chinensis* Franch., (B16) the leaf of *cordia spinescens*, (B17) the rhizome of *Cyrtomium fortunei* J. Sm., (B18) the rhizome of *Drynaria fortunei* (Kunze) J. Smith, (B19) the rhizone of *Dryopteris crassirhizoma* Nakai, (B20) the fruit of *Elaeocarpus grandiflorus* Smith, (B21) the leaf of *Epimedium koreanum* Nakai, (B22) the leaf of *Erythroxylum lucidum*, (B22') the trunk of *Erythroxylum citrifolium*, (B23) the fruit of *Foeniculum vulgare* Mill., (B24) the whole plant of *Geranium thunbergii* Sieb. et Zucc., (B25) the whole plant of *Geum japonicum* Thunb., (B26) the leaf of *Hamelia axillaris* Swartz, (B27) the branch and leaf of *Jatropha curcas* L., (B28) the bark of *Juglans mandshurica* Maxim., (B29) the bark of *Machilus thunbergii* Sieb. et Zucc., (B30) the root bark of *Paeonia suffruticosa* Andrews, (B31) the leaf of *Perilla frutescens* Britton var. acuta Kudo, (B32) the bark of *Phellodendron amurense* Ruprecht, (B33) the rhizome of *Plagiogyria matsumureana* Makino, (B34) the root of *Polygala tenuifolia* Willd., (B35) the root and rhizome of *Polygonum cuspidatum* Sieb. et Zucc., (B36) the spike of *Prunella vulgaris* L. subsp. asiatica Hara, (B37) the root bark and fruit peel of *Punica granatum* L., (B38) the bark of *Quercus acutissima* Carruthers, (B39) the rhizome of *Rheum palmatum* L., (B40) the gall of *Rhus javanica* L., (B41) the root of *Salvia miltiorrhiza* Bunge, (B42) the leaf of *Sarcandra glabra* (Thunb.) Nakai, (B43) the flores of *Schizonepeta tenuifolia* Briquet, (B44) the whole plant of *Serjania mexicana*, (B45) the stem of *Spatholobus suberectus* Dunn, (B46) the bark of *Terminalia arjuna* Wight et Arn., (B47) the fruit peel of *Terminalia belerica* Roxb., (B48) the fruit of *Terminalia chebula* Retzus, (B49) the branch and leaf of *Waltheria indica* L., (B50) the flower and leaf of *Woodfordia floribunda* Salisb., (B51) the rhizome of *Woodwardia orientalis* Sw., and (B52) the fruit peel of *Zanthoxylum bungeanum* Maxim. (hereinafter referred to as group B).

The second embodiment of the present invention relates to an antipolioviral agent containing at least one crude drug selected from the group consisting of (C1) the rhizome of *Alpinia officinarum* Hance, (C2) the bark of *Andrographis paniculate* Nees, (C3) the root of *Andropogon zizaniodes* (L.) Urban, (C4) the rhizome of *Anemarrhena asphodeloides* Bunge, (C5) the leaf of *Arctostaphylos uva-ursi* (L.) Sprengel, (C6) the seed of *Areca catechu* L., (C7) the leaf of *Artemisia princeps* Pamp., (C8) the whole plant of *Asiasarum heterotropoides* F. Maekawa var. mandshuricum F. Maekawa, (C9) the rhizome of *Belamcanda chinensis* (L.) DC., (C10) the rhizome of *Brainia insignis* (Hook.) J. Sm., (C11) the seed of *Brucea javanica* (L.) Merr, (C12) the bark of *Caesalpinia sappan* L., (C13) the bark of *Cassia fistula* L., (C14) the bark of *Cinnamomum sintok* Blume, (C15) the rhizome of *Coptis chinensis* Franch., (C16) the fruit of *Cornus officinalis* Sieb. et Zucc., (C17) the tuber of *Corydalis hurtscharinorii* Besser forma yanhusuo Y. H. Chou et C. C. Hsu, (C18) the fruit of *Curculigo orchioides* Gaertn., (C19) the rhizome of *Curcuma aeroginosa* Roxb., (C20) the rhizome of *Curcuma xanthorrhiza* Roxb., (C21) the rhizome of *Cyrtomium fortunei* J. Sm., (C22) the rhizome of *Dryopteris crassirhizoma* Nakai, (C23) the fruit of *Elaeocarpus grandiflorus* Smith, (C24) the leaf of *Elephantopus scaber* L., (C25) the fruit of *Eyodia rutaecarpa* Hook. f. et Thoms., (C26) the fruit of *Foeniculum vulgare* Mill., (C27) the fruit of *Forsythia suspensa* Vahl., (C28) the whole plant of *Geranium thunbergii* Sieb. et Zucc., (C29) the whole plant of *Geum japonicum* Thunb., (C30) the bark of *Juglans mandshurica* Maxim., (C31) the root of *Lithospermum erythrorhizon* Sieb. et Zucc., (C32) the aerial part of *Loranthus parasiticus* (L.) Merr., (C33) the bark of *Machilus thunbergii* Sieb. et Zucc., (C34) the rhizome of *Matteuccia struthiopteris* (L.) Todaro, (C35) the whole insect of *Mylabris sidae* Fabr., (C36) the root bark of *Paeonia suffruticosa* Andrews, (C37) the bark of *Parameria laevigata* Moldenke, (C38) the bark of *Phellodendron amurense* Ruprecht, (C39) the aerial part of *Physalis angulata* L., (C40) the rhizome of *Plagiogyria matsumureana* Makino, (C41) the root of *Polygala tenuifolia* Willd., (C42) the root and rhizome of *Polygonum cuspidatum* Sieb. et Zucc., (C43) the bark of *Prunus jamasakura* Siebold, (C44) the fruit of *Prunus mume* Sieb. et Zucc., (C45) the root bark and fruit peel of *Punica granatum* L., (C46) the bark of *Quercus acutissima* Carruthers, (C47) the leaf of *Quercus salicina* Blume, (C48) the fruit of *Quisgualis indica* L., (C49) the rhizome of *Rheum palmatum* L., (C50) the gall of *Rhus javanica* L., (C51) the root of *Scutellaria baicalensis* Georgi, (C52) the flower bud of *Sophora japonica* L., (C53) the root of *Sophora subprostrata* Chun et T. Chen, (C54) the stem of *Spatholobus suberectus* Dunn, (C55) the rhizome of *Struthiopteris niponica* (Kunze) Nakai, (C56) the seed of *Strychnos nux-vomica* L., (C57) the flower bud of *Syzygium aromaticum* (L.) Merr. et Perry, (C58) the bark of *Terminalia arjuna* Wight et Arn., (C59) the fruit peel of *Terminalia belerica* Roxb., (C60) the fruit of *Terminalia chebula* Retzus, (C61) the leaf and branch of *Uncaria gambir* Roxb., (C62) the whole plant of *Usnea misaminensis* Vain., (C63) the flower and leaf of *Woodfordia floribunda* Salisb., (C64) the rhizome of *Woodwardia orientalis* Sw., and (C65) the fruit peel of *Zanthoxylum bungeanum* Maxim. (hereinafter referred to as group C).

The third embodiment of the present invention relates to an anti-measles virus agent containing at least one crude drug selected from the group consisting of (D1) the seed of *Areca catechu* L., (D2) the leaf of *Artemisia princeps* Pamp., (D3) the rhizome of *Belamcanda chinensis* (L.) DC., (D4) the rhizome of *Brainia insignis* (Hook.) J. Sm., (D5) the seed of *Brucea javanica* (L.) Merr, (D6) the bark of *Caesalpinia sappan* L., (D7) the bark of *Cassia fistula* L., (D8) the bark of *Cinnamomum sintok* Blume, (D9) the rhizome of *Cnidium officinale* Makino, (D10) the rhizome of *Coptis chinensis* Franch., (D11) the rhizome of *Cyrtomium fortunei* J. Sm., (D12) the fruit of *Elaeocarpus grandiflorus* Smith, (D13) the leaf of *Elephantopus scaber* L., (D14) the fruit of *Foeniculum vulgare* Mill., (D15) the fruit of *Forsythia suspensa* Vahl., (D16) the whole plant of *Geranium thunbergii* Sieb. et Zucc., (D17) the root and stolon of *Glycyrrhiza uralensis* Fisher, (D18) the bark of *Juglans mandshurica* Maxim., (D19) the bark of *Magnolia officinalis* Rehd. et Wils., (D20) the whole insect of *Mylabris sidae* Fabr., (D21) the root bark of *Paeonia suffruticosa* Andrews, (D22) the bark of *Phellodendron amurense* Ruprecht, (D23) the rhizome of *Plagiogyria matsumureana* Makino, (D24) the root of *Platycodon grandiflorum* (Jacquin) A. DC., (D25) the root of *Polygala tenuifolia* Willd., (D26) the root bark and fruit peel of *Punica granatum* L., (D27) the bark of *Quercus acutissima* Carruthers, (D28) the rhizome of *Rheum palmatum* L., (D29) the gall of *Rhus javanica* L., (D30) the root of *Scutellaria baicalensis* Georgi, (D31) the stem of *Spatholobus suberectus* Dunn, (D32) the flower bud of *Syzygium aromaticum* (L.) Merr. et Perry, (D33) the bark of *Terminalia arjuna* Wight et Arn., (D34) the fruit peel of *Terminalia belerica* Roxb., (D35) the fruit of *Terminalia chebula* Retzus, (D36) the flower and leaf of *Woodfordia floribunda* Salisb., (D37) the rhizome of *Woodwardia orientalis* Sw., and (D38) the fruit of *Zizyphus jujuba* Miller var. inermis Rehder (hereinafter referred to as group D).

The forth embodiment of the present invention relates to an anti-varicella-zoster virus agent containing at least one crude drug selected from the group consisting of (E1) the rhizome of *Alpinia officinarum* Hance, (E2) the seed of *Areca catechu* L., (E3) the leaf of *Artemisia princeps* Pamp., (E4) the root of *Bupleurum fakatum* L., (E5) the bark of *Cassia fistula* L., (E6) the rhizome of *Coptis chinensis* Franch., (E7) the rhizome of *Cyrtomium fortunei* J. Sm., (E8) the rhizome of *Drynaria fortunei* (Kunze) J. Smith., (E9) the whole plant of *Geranium thunbergii* Sieb. et Zucc., (E10) the root and stolon of *Glycyrrhiza uralensis* Fisher, (E11) the bark of *Juglans mandshurica* Maxim., (E12) the root bark of *Paeonia suffruticosa* Andrews, (E13) the root of *Panax ginseng* C. A. Meyer, (E14) the bark of *Phellodendron amurense* Ruprecht, (E15) the rhizome of *Plagiogyria matsumureana* Makino, (E16) the root of *Polygala tenuifolia* Willd., (E17) the root and rhizome of *Polygonum cuspidatum* Sieb. et Zucc., (E18) the hoelen of *Poria cocos* Wolf, (E19) the root bark and fruit peel of *Punica granatum* L., (E20) the bark of *Quercus acutissim* Carruthers, (E21) the rhizome of *Rheum palmatum* L., (E22) the gall of *Rhus javanica* L., (E23) the flower bud of *Syzygium aromaticum* (L.) Merr. et Perry, (E24) the bark of *Terminalia arjuna* Wight et Arn., (E25) the fruit of *Terminalia chebula* Retzus, (E26) the rhizome of *Woodwardia orientalis* Sw., and (E27) the rhizome of *Dryopteris crassirhizoma* Nakai (hereinafter referred to as group E).

The fifth embodiment of the present invention relates to an anti-CMV agent containing at least one crude drug selected from the group consisting of (F1) the seed of *Areca catechu* L., (F2) theleaf of *Artemisia princeps* Pamp., (F3) the bark of *Cassia fistula* L., (F4) the rhizome of *Coptis chinensis* Franch., (F5) the rhizome of *Cyrtomium fortunei* J. Sm., (F6) the rhizome of *Drynaria fortunei* (Kunze) J. Smith, (F7) the whole plant of *Geranium thunbergii* Sieb. et Zucc., (F8) the whole plant of *Geum japonicum* Thunb., (F9) the bark of *Juglans mandshurica* Maxim., (F10) the bark of *Machilus thunbergii* Sieb. et Zucc., (F11) the root bark of *Paeonia suffruticosa* Andrews, (F12) the bark of *Phellodendron amurense* Ruprecht, (F13) the rhizome of *Plagiogyria matsumureana* Makino, (F14) the root of *Polygala tenuifolia* Willd., (F15) the root and rhizome of *Polygonum cuspidatum* Sieb. et Zucc., (F16) the root bark and fruit peel of *Punica granatum* L., (F17) the bark of *Quercus acutissima* Carruthers, (F18) the rhizome of *Rheum palmatum* L., (F19) the gall of *Rhus javanica* L., (F20) the flower bud of *Syzygium aromaticum* (L.) Merr. et Perry, (F21) the bark of *Terminalia arjuna* Wight et Arn., (F22) the fruit of *Terminalia chebula* Retzus, and (F23) the rhizome of *Woodwardia orientalis* Sw. (hereinafter referred to as group F).

The sixth embodiment of the present invention relates to an anti-DNA virus and anti-RNA virus agent containing at least one crude drug selected from the group consisting of (G1) the seed of *Areca catechu* L., (G2) the leaf of *Artemisia princeps* Pamp., (G3) the rhizome of *Brainia insignis* (Hook.) J. Sm., (G4) the seed of *Brucea javanica (L.) Merr., (G5) the bark of Caesalpinia sappan* L., (G6) the bark of *Cassia fistula* L., (G7) the bark of *Cinnamomum sintok* Blume, (G8) the rhizome of *Coptis chinensis* Franch., (G9) the rhizome of *Cyrtomium fortunei* J. Sm., (G10) the fruit of *Elaeocarpus grandiflorus* Smith, (G11) the fruit of *Foeniculum vulgare* Mill., (G12) the whole plant of *Geranium thunbergii* Sieb. et Zucc., (G13) the bark of *Juglans mandshurica* Maxim., (G14) the root bark of *Paeonia suffruticosa* Andrews, (G15) the bark of *Phellodendron amurense* Ruprecht, (G16) the rhizome of *Plagiogyria matsumureana* Makino, (G17) the root of *Polygala tenuifolia* Willd., (G18) the root bark and fruit peel of *Punica granatum* L., (G19) the bark of *Quercus acutissima* Carruthers, (G20) the rhizome of *Rheum palmatum* L., (G21) the gall of *Rhus javanica* L., (G22) the stem of *Spatholobus suberectus* Dunn, (G23) the flower bud of *Syzygium aromaticum* (L.) Merr. et Perry, (G24) the bark of *Terminalia arjuna* Wight et Arn., (G25) the fruit peel of *Terminalia belerica* Roxb., (G26) the fruit of *Terminalia chebula* Retzus, (G27) the flower and leaf of *Woodfordia floribunda* Salisb., (G28) the rhizome of *Woodwardia orientalis* Sw. (hereinafter referred to as group G).

The seventh embodiment of the present invention relates to an antiherpesviral agent containing at least one crude drug selected from the group B as mentioned above and the other antiviral agent.

DETAILED DESCRIPTION OF THE INVENTION

All viruses are classified into DNA viruses and RNA viruses. Families included inder DNA viruses include Poxviridae, Herpesviridae, Adenoviridae, Papovaviridae, Hepadnaviridae, and Parvoviridae. Familes included under RNA viruses include Reoviridae, Picornaviridae, Togaviridae, Flaviviridae, Coronaviridae, Rhabdoviridae, Paramyxoviridae, Orthomyxoviridae, Filoviridae, Bunyaviridae, Arenaviridae, Caliciviridae and Retroviridae.

Familes belonging to DNA viruses have many basic traits in common in DNA replication mechanism. RNA viruses also have characteristics in common with each other in the growth step. The common characteristics include a number of cell-dependent DNA replication-related enzymes, complementarily acting cell factors, and RNA synthesis by RNA dependent RNA polymerase (RNA replicase), and so on. Therefore, a drug exhibiting inhibitory activity on proliferation of a typical DNA virus, e.g., the Herepesviridae, or a typical RNA virus, e.g., the Picornaviridae, is expected to be effective as an antiviral agent common to a wide range of DNA or RNA viruses.

Viruses belonging to Picornaviridae include poliovirus, echovirus, coxsackie virus, enterovirus, and rhinovirus. Diseases caused by these viruses include acute anterior poliomyelitis, hand-foot-and-mouth disease, herpangina, myopericarditis, epidermic myalgia, enanthema, acute hemorrhagic conjuctivitis, summer cold, aseptic meningitis, hepatitis type A, coryza, respirator infectious diseases, and the like.

Viruses-zoster belonging to Paramyxoviridae include parainfluenze virus, mumps virus, measles virus, and RS virus. Diseases caused by these viruses include pharyngitis, upper respiratory tract infectious disease, bronchitis, pneumonia, measles, mumps, and acute respiratory tract infectious disease.

Varicella virus belongs to the family Herpesviridae and causes varicella in children aged between 2 and 8 easily by droplet infection or contagen. Herpes zoster mostly occurs in adults having once suffered from varicella and aged over 50.

CMV also belongs to the family Herpesviridae. Besides the above-mentioned problem, if a woman is first infected with CMV during pregnancy, it sometimes happens that the fetus is directly infected to develop congenital cytomegalic inclusion body disease, etc. Further, CMV often plays a main role in opportunistic infection in acquired immunodeficiency syndrome (AIDS).

The crude drugs belonging to group B have antiherpesviral activity; those of group C antipolioviral activity; those of group D anti-measles virus activity; those of group E anti-varicella-zoster virus activity; those of group F anti-CMV activity; and those of group G anti-DNA virus and anti-RNA virus activity. Group A includes all crude drugs of the present invention.

The dosage, administration route, etc. of the crude drugs included under group A, inclusive of groups B to G, are well known, and the known dose levels produce no or slight side effects.

2 to 10 g of the crude drug according to the present invention is added to water at a ratio of 50 ml water per g of the crude drug, and the mixture is boiled and concentrated to half the original volume. The resulting extract can be orally administered three times a day at a dose of one-third of the extract.

In particular, as hereinafter described, when at least one of the crude drugs of group B is used in combination of acyclovir, a known antiviral agent, there is produced synergistic antiviral activity, by which the requisite dose of acyclovir can be reduced, and appearance of acyclovir-resistant viruses will be inhibited.

Accordingly, the crude drug according to the present invention whose fraction having been absorbed through the digestive tracts exhibits antiviral activity, or a combination of such a crude drug and other known antiviral agent is considered effective in prevention and treatment of the above-mentioned diseases caused by herpes simplex virus (e.g., herpes simplex and its complication), diseases caused by varicella-zoster virus (e.g., varicella, shingles and complications thereof), and diseases caused by CMV (e.g., pneumonia, hepatitis, and conjuctivitis).

Test Examples of the present invention are described below. All the plants and insects used in the tests were purchased at the market. The part of the plants or insects used was as described above.

Preparation of Extract

Each plant or insect was extracted at reflux with distilled water under a neutral condition, followed by concentration and drying to obtain an aqueous extract of the crude drug. It is generally spread to use methanol in place of water as an extracting solvent for obtaining hydrophobic substances in higher concentrations. The test of antiviral activity was also conducted on the methanol extract of some of crude drugs.

For example, 100 g of the rhizome of Cyrtomium fortunei J. Sm.# (available on the Hong Kong market) was extracted at reflux with 1.5 l of distilled water, and the extract was concentrated at 40° C. under reduced pressure and lyophilized to obtain 12.3 g of an aqueous extract of Cyrtomium fortunei J. Sm.# (the term "extract" hereinafter used means an aqueous extract unless otherwise specified). Cyrtomium fortunei J. Sm. with a sharp mark means a mixture of Brainia insignis (Hook.) J. Sm., Cyrtonium fortunei J. Sm., Dryopteris crassirhizoma Nakai, Matteuccia struthiopteris (L.) Todaro, Plagiogyria matsumureana Makino, Struthiopteris niponica (Kunze) Nakai and Woodwardia orientalis Sw. The Cyrtomium fortunei J. Sm.# is available on the Hong Kong market.

A methanol extract was obtained by, for example, extracting 20 g of a crude drug with 500 ml. of methanol for 3 hours and removing methanol by distillation under reduced pressure.

Each crude drug extract was ground and suspended in water in a prescribed concentration. The suspension was heated in a boiling water bath for 10 minutes and centrifuged (3000 rpm×10 min.). The resulting supernatant, an extract solution, was used for the antiviral test.

Test Virus

Herpes simplex virus type I (Seibert strain), poliovirus (vaccine strain and Sabin strain), measles virus (vaccine strain and Tanabe strain), varicella-zoster virus (Kawaguchi strain), and CMV (Town strain) were used.

Vero cells or HEL cells derived from human embryonal lungs were infected with each virus except varicella-zoster virus. After incubation for a prescribed time, the infected cells were subjected to freezing and thawing three times, followed by centrifugation (300 rpm×15 mins.). The supernatant was used as a virus suspension.

A varicella-zoster virus suspension was prepared according to the method of Shiraki K and Takahashi M., J. Gen. Virol., vol 61, pp. 271–275, "Virus particles and glycoproteines excreted from cultured cells infected with varicella-zoster virus".

The thus prepared virus liquids were preserved, if necessary, at −80° C.

Cells to be Infected with Virus

1. Vero cells originated from the kidney of African green monkey were cultured in a minimum essential medium (hereinafter abbreviated as MEM) containing 5% bovine fetal serum (BFS).
2. Vero E6 cells were obtained by cloning of the above-mentioned Vero cells and have high susceptibility to infection with various viruses.
3. HEL cells originated from human embryonal lungs which have high susceptibility to infection with varicella-zoster virus and CMV.

Cultivation of all these cells were conducted in $CO_2$ incubator at 37° C.

Plague Formation Test Method 0.2 ml of a virus suspension diluted to 100 PFU/0.2 ml was inoculated to a monolayer culture of Vero cells, Vero E6 cells or HEL cells in a plastic dish having a diameter of 60 mm. The virus was allowed to adsorb on the monolayer cells at 37° C. for 1 hour.

After adsorption, 5 ml of 2% BFS-added MEM containing each extract solution in a prescribed concentration and 0.8% methyl cellulose was plied on the monolayer cells, and the system was cultured at 37° C. for 2 to 5 days to observe plaque formation. The cultured monolayer cells were fixed with formalin and stained with a 0.03%-Methylene Blue solution for measuring the number of plaques.

Where the above-mentioned test was replicated several times with the same concentration of the extract solution, the results obtained sometimes show slight scatter. This seems attributed to the error in detection and judgement of plaques due to slight variation of susceptibility depending on the cultivation conditions, such as the lot of serum, the culture plate, the cell density, etc.

TEST EXAMPLE 1

Antiherpesviral activity of the crude drugs shown in Table 1 at a concentration shown were examined by using Vero cells or Vero E6 cells by the plaque formation test. The results obtained are shown in Table 1 below. It can be seen from the Table that the extract of the crude drug according to the present invention significantly reduced the efficiency of plaque formation at such a concentration as low as 500 μg/ml or less and thus exhibited herpesvirus growth inhibitory activity.

TABLE 1

| | | Antiherpesviral Activity | | |
|---|---|---|---|---|
| | | Plaque Formation Efficiency (%) | | |
| Species | Part | 100 μm/ml | 300 μm/ml | 500 μm/ml |
| (B1)*Ainsliaea fragrans* Champ. | whole plant | 55.7 | 51.7 | |
| (B2)*Alpinia officinarum* Hance | rhizome | 106.8 | 0 | |
| (B3)*Alyxia stellata* Roem. | bark | 59.8 | 57.9 | |
| (B4)*Andropogon zizaniodes* (L.) Urban | root | 73.8 | 39.3 | |
| (B5)*Areca catechu* L. | seed | 0 | | 0 |
| (B6)*Artemisia princeps* Pamp. | leaf | 65 | | 0 |
| (B7)*Brainia insignia* (Hook.) J. Sm. | rhizome | 62.7 | 0 | |
| (B8)*Brucea jayanica* (L.) Merr. | seed | 6.3 | 0 | |
| (B9)*Caesalpinia sappan* L. | bark | 0 | 0 | |
| (B10)*Camellia japonica* L. | leaf | 89.7 | 54.8 | |
| (B11)*Cassia fistula* L. | bark | 67 | 0 | |
| (B12)*Chamaesyce hyssopifolia* | whole plant | 35.6 | | |
| (B13)*Cinnamomum cassia* Blume | bark, branch | 69.5 | 21.5 | |
| (B14)*Cinnamomum sintok* Blume | bark | 0 | 0 | |
| (B15)*Coptis chinensis* Franch. | rhizome | 74.1 | 0 | |
| (B16)*Cordia spinescens* | leaf | 6 | | |
| (B17)*Cyrtomium fortunei* J. Sm. | rhizome | 59.6 | 0 | |
| (B18)*Drynaria fortunei* (Kunze) J. Smith | rhizome | 87.4 | 0 | |
| (B19)*Dryopteris crassirhizoma* Nakai | rhizome | 62.1 | 51.7 | |
| (B20)*Elaeocarpus grandiflorus* Smith | fruit | 0 | 0 | |
| (B21)*Epimedium koreanum* Nakai | leaf | 65.1 | 42.3 | |
| (B22)*Erythroxylum citrifolium* | trunk | 33.6 | | |
| (B22')*Erythroxylum lucidum* | leaf | 41.8 | | |
| (B23)*Foeniculum vulgare* Mill. | fruit | 67.5 | 47.5 | |
| (B24)*Geranium thunbergii* Sieb. et Zucc. | whole plant | 91.6 | 23.5 | |
| (B25)*Geum japonicum* Thunb. | whole plant | 81.7 | | 0 |
| (B26)*Hamelia axillaris* Swartz | leaf | 35.3 | | |
| (B27)*Jatropha curcas* L. | branch, leaf | 32 | | |
| (B28)*Juglans mandshurica* Maxim. | bark | 73.6 | 0 | |
| (B29)*Machilus thunbergii* Sieb. et Zucc. | bark | 98.6 | 17.8 | |
| (B30)*Paeonia suffruticosa* Andrews | root bark | 96.5 | | 0 |
| (B31)*Perilla frutescens* Britton var. acuta Kubo | leaf | 67.2 | 45.2 | |
| (B32)*Phellodendron amurense* Ruprecht | bark | 85.3 | | 29.4 |
| (B33)*Plagiogyria matsumureana* Makino | rhizome | 76.1 | 50.7 | |
| (B34)*Polygala tenuifolia* Willd. | root | 118.6 | | 0 |
| (B35)*Polygonum cuspidatum* Sieb. et Zucc. | root, rhizome | 93.4 | | 0 |
| (B36)*Prunella vulgaris* L. subsp. asiatica Hara | spike | 66.1 | | 0 |
| (B37)*Punica granatum* L. | root bark, fruit peel | 0 | | 0 |
| (B38)*Quercus acutissima* Carruthers | bark | 38.2 | 9.8 | |
| (B39)*Rheum palmatum* L. | rhizome | 93.2 | 0 | |
| (B40)*Rhus javanica* L. | gall | 0 | | 0 |
| (B41)*Salvia miltiorrhiza* Bunge | root | 89.9 | | 58.6 |
| (B42)*Sarcandra glabra* (Thunb.) Nakai | leaf | 67.7 | 51.6 | |
| (B43)*Schizonepeta tenuifolia* Briquet | flores | 73.8 | 48.4 | |
| (B44)*Serjania mexicana* | whole plant | 37.6 | | |
| (B45)*Spatholobus suberectus* Dunn | stem | 92.2 | 0 | |
| (B46)*Terminalia arjuna* Wight et Arn. | bark | 56.3 | 0 | |
| (B47)*Terminalia belerica* Roxb. | fruit peel | 70.8 | 0 | |
| (B48)*Terminalia chebula* Retzus | fruit | 99.6 | | 0 |
| (B49)*Waltheria indica* L. | branch, leaf | 27.2 | | |
| (B50)*Woodfordia floribunda* Salisb. | flower, leaf | 0 | 0 | |
| (B51)*Woodwardia orientalis* Sw. | rhizome | 51.6 | 0 | |
| (B52)*Zanthoxylum bungeanum* Maxim. | fruit peel | 107.7 | 20.3 | |

TEST EXAMPLE 2

Antipolioviral activity of the crude drugs shown in Table 2 (group C) was determined in the same manner as in Test Example 1. The results are shown in the Table.

The crude drug extract solution shown in Table 2 showed cytotoxicity at a concentration of about 300μg/ml or 500 μg/ml. However, from the fact that these crude drugs have been orally administered for years with no or only slight side effects observed, cytotoxicity of these crude drugs appears to give rise to no problem.

Through screening various crude drugs for antiviral activity against poliovirus as a typical species of the viruses belonging to the family Picornaviridae as described above, medicines having antiviral activity against viruses belonging to Picornaviridae and having the similar physicochemical properties and proliferation mechanism in common can be developed.

The crude drugs belonging to group C whose fraction absorbed through the digestive tract exhibits antiviral activity against poliovirus are considered effective for prevention and treatment of the diseases caused by viruses belonging to the family Picornaviridae.

TABLE 2

| Antipolioviral Acitivity | | | | |
|---|---|---|---|---|
| | | Plaque Formation Efficiency (%) | | |
| Species | Part | 100 μm/ml | 300 μm/ml | 500 μm/ml |
| (C1)*Alpinia officinarum* Hance | rhizome | 58.9 | 11.5 | |
| (C2)*Andrographis paniculate* Nees | bark | 88.1 | 55.1 | |
| (C3)*Andropogon zizaniodes* (L.) Urban | root | 19.5 | 7.6 | |
| (C4)*Anemarrhena asphodeloides* Bunge | rhizome | 44.2 | | 30.1 |
| (C5)*Arctostaphylos uva-ursi* (L.) Sprengel | leaf | 63.3 | 54.6 | |
| (C6)*Areca catechu* L. | seed | 86.5 | | $0^{+}$ |
| (C7)*Artemisia princeps* Pamp. | leaf | 84.3 | | 40.5 |
| (C8)*Asiasarum heterotropoides* F. Maekawa var. mandshuricum F. Maekawa | whole plant | 73.2 | | 43 |
| (C9)*Belamcanda chinensis* (L.) DC. | rhizome | 97.4 | | 55.1 |
| (C10)*Brainia insignis* (Hook.) J. Sm. | rhizome | 61 | 54.6 | |
| (C11)*Brucea javanica* (L.) Merr. | seed | 0 | 0 | |
| (C12)*Caesalpinia sappan* L. | bark | 0 | $0^{+}$ | |
| (C13)*Cassia fistula* L. | bark | 52.1 | 2.8 | |
| (C14)*Cinnamomum sintok* Blume | bark | 102.5 | $0^{+}$ | |
| (C15)*Coptis chinensis* Franch. | rhizome | 89.7 | | 0 |
| (C16)*Cornus officinalis* Sieb. et Zucc. | fruit | 82.2 | | 57.2 |
| (C17)*Corydalis hurtscharinorii* Besser forma yanhusuo Y. H. Chou et C. C. Hsu | tuber | 77.4 | | 6.4 |
| (C18)*Curculigo orchioides* Gaertn. | fruit | 88.1 | 42.4 | |
| (C19)*Curcuma aeroginosa* Roxb. | rhizome | 34 | 29.7 | |
| (C20)*Curcuma xanthorrhiza* Roxb. | rhizome | 39 | 35.6 | |
| (C21)*Cyrtomium fortunei* J. Sm. | rhizome | 66.5 | $0^{+}$ | |
| (C22)*Dryopteris crassirhizoma* Nakai | rhizome | 93.8 | 48.4 | |
| (C23)*Elaeocarpus grandifluorus* Smith | fruit | 0 | 0 | |
| (C24)*Elephantopus scaber* L. | leaf | 20.8 | 17.7 | |
| (C25)*Evodia rutaecarpa* Hook. f. et Thoms. | fruit | 82.1 | 41.1 | |
| (C26)*Foeniculum vulgare* Mill. | fruit | 31.3 | 28.1 | |
| (C27)*Forsythia suspensa* Vahl. | fruit | 72.9 | | 30.7 |
| (C28)Geranium thunbergii Sieb. et Zucc. | whole plant | 30 | 21.4 | |
| (C29)*Geum japonicum* Thunb. | whole plant | 90.4 | | 0 |
| (C30)*Juglans nandshurica* Maxim. | bark | 35.5 | 4.8 | |
| (C31)*Lithospermum erythrorhizon* Sieb. et Zucc. | root | 61.9 | 50 | |
| (C32)*Loranthus parasiticus* (L.) Merr. | aerial part | 83.3 | 29.2 | |
| (C33)*Machilus thunbergii* Sieb. et Zucc. | bark | 55.5 | 0 | |
| (C34)*Matteuccia struthiopteris* (L.) Todaro | rhizome | 65.9 | 34.6 | |
| (C35)*Mylabris sidae* Fabr. | whole insect | 88.4 | $0^{+}$ | |
| (C36)*Paeonia suffruticosa* Andrews | root bark | 124.2 | | 35.5 |
| (C37)*Parameria laevigata* Moldenke | bark | 43.8 | 32.3 | |
| (C38)*Phellodendron amurense* Ruprecht | bark | 103.4 | | 43.3 |
| (C39)*Physalis angulata* L. | aerial part | 17.6 | 0 | |
| (C40)*Plagiogyria matsumureana* Makino | rhizome | 73.9 | 0 | |
| (C41)*Polygala tenuifolia* Willd. | root | 86.4 | | $0^{+}$ |
| (C42)*Polygonum cuspidatum* Sieb. et Zucc. | root, rhizome | 88 | | 38 |
| (C43)*Prunus jamasakura* Siebold | bark | 99.7 | 46.9 | |
| (C44)*Prunus mume* Sieb. et Zucc. | fruit | 75.8 | 38.9 | |
| (C45)*Punica granatum* L. | root bark, fruit peel | 79.5 | | 0 |
| (C46)*Quercus acutissima* Carruthers | bark | 98.4 | 35.6 | |
| (C47)*Quercus salicina* Blume | leaf | 48 | 30.6 | |
| (C48)*Quisqualis indica* L. | fruit | 28.2 | 16.9 | |
| (C49)*Rheum palmatum* L. | rhizome | 13.1 | $0^{+}$ | |
| (C50)*Rhus javanica* L. | gall | 65.1 | | 4.3 |
| (C51)*Scutellaria baicalensis* Georgi | root | 66 | | 14.7 |
| (C52)*Sophora japonica* L. | flower bud | 67.1 | 49.5 | |
| (C53)*Sophora subprostrata* Chun et T. Chen | root | 99.5 | | 57.7 |
| (C54)*Spatholobus suberectus* Dunn | stem | 80.2 | 0 | |
| (C55)*Struthiopteris niponica* (Kunze) Nakai | rhizome | 66 | 33.4 | |
| (C56)*Strychnos nux-vomica* L. | seed | 39.6 | 47.9 | |
| (C57)*Syzygium aromaticum* (L.) Merr. et Perry | flower bud | 55.1 | $0^{+}$ | |
| (C58)*Terminalia arjuna* Wight et Arn. | bark | 22.5 | 0 | |
| (C59)*Terminalia belerica Roxb.* | fruit peel | 7.4 | 0 | |
| (C60)*Terminalla chebula* Retzus | fruit | 32.6 | 0.7 | |
| (C61)*Uncaria gambir* Roxb. | leaf, branch | 85.3 | 24.2 | |
| (C62)*Usnea misaminensis* Vain. | whole plant | 111.1 | 53.7 | |

TABLE 2-continued

| | Antipolioviral Acitivity | | | |
|---|---|---|---|---|
| | | Plaque Formation Efficiency (%) | | |
| Species | Part | 100 μm/ml | 300 μm/ml | 500 μm/ml |
| (C63)*Woodfordia floribunda* Salisb. | flower, leaf | 0 | 0+ | |
| (C64)*Woodwardia orientalis* Sw. | rhizome | 30.5 | 0+ | |
| (C65)*Zanthoxylum bungeanum* Maxim. | fruit peel | 80.4 | | 14.3 |

Note:
+: Cytotoxicity was observed.

TEST EXAMPLE 3

Anti-measles virus activity of the crude drugs shown in Table 3 (group D) was determined in the same manner as in Test Example 1. The results obtained are shown in Table 3. The crude drugs belonging to group D were thus proved to have anti-measles virus activity.

Through screening various crude drugs for antiviral activity against measle virus as a typical species of the viruses belonging to the family Paramyxoviridae as described above, medicines having antiviral activity against viruses belonging to Paramyxoviridae and having the similar physicochemical properties and proliferation mechanism in common can be developed.

The crude drugs belonging to group D whose fraction absorbed through the digestive tract exhibits antiviral activity against measle virus are considered effective for prevention and treatment of the diseases caused by viruses belonging to the family Paramyxoviridae.

TABLE 3

| Anti-measle Virus Activity | | | | |
|---|---|---|---|---|
| | | Plaque Formation Efficiency (%) | | |
| Species | Part | 100 μm/ml | 300 μm/ml | 500 μm/ml |
| (D1) *Areca catechu* L. | seed | 93.6 | | 0 |
| (D2) *Artemisia princeps* Pamp. | leaf | 10.8 | | 13.6 |
| (D3) *Belamcanda chinensis* (L.) DC. | rhizome | 100 | | 0 |
| (D4) *Brainia insignis* (Hook.) J. Sm. | rhizome | 109.7 | 5.1 | |
| (D5) *Brucea javanica* (L.) Merr. | seed | 37.2 | 0 | |
| (D6) *Caesalpinia sappan* L. | bark | 0 | 0 | |
| (D7) *Cassia fistula* L. | bark | 100 | 14.1 | |
| (D8) *Cinnamomum sintok* Blume | bark | 153 | 0 | |
| (D9) *Cnidium officinale* Makino | rhizome | 64.1 | 43.5 | |
| (D10) *Coptis chinensis* Franch. | rhizome | 5.6 | | 0 |
| (D11) *Cyrtomium fortunei* J. Sm. | rhizome | 112.1 | 0 | |
| (D12) *Elaeocarpus grandiflorus* Smith | fruit | 0 | 0 | |
| (D13) *Elephantopus scaber* L. | leaf | 85 | 47.8 | |
| (D14) *Foeniculum vulgare* Mill. | fruit | 99.3 | 47.5 | |
| (D15) *Forsythia suspensa* Vahl. | fruit | 26.1 | | 6.7 |
| (D16) *Geranium thunbergii* Sieb. et Zucc. | whole plant | 104.7 | 0 | |
| (D17) *Glycyrrhiza uralensis* Fischer | root, stolon | 59.4 | 50 | |
| (D18) *Juglans mandshurica* Maxim. | bark | 96.5 | 3.5 | |
| (D19) *Magnolia officinalis* Rehd. et Wils. | bark | 71.6 | 34.1 | |
| (D20) *Mylabris sidae* Fabr. | whole insect | 60.2 | 0 | |
| (D21) *Paeonia suffruticosa* Andrews | root bark | 119.1 | | 0 |
| (D22) *Phellodendron amurense* Ruprecht | bark | 17.2 | | 0.6 |
| (D23) *Plagiogyria matsumureana* Makino | rhizome | 90.8 | 84.6 | |
| (D24) *Platycodon grandiflorum* (Jacquin) A. DC. | root | 95.1 | 0 | |
| (D25) *Polygala tenuifolia* Willd. | root | 100 | | 0 |
| (D26) *Punica granatum* L. | root bark, fruit peel | 0 | | 0 |
| (D27) *Quercus acutissima* Carruthers | bark | 83.3 | 38.5 | |
| (D28) *Rheum palmatum* L. | rhizome | 108.1 | 0 | |
| (D29) *Rhus javanica* L. | gall | 3.4 | | 0 |
| (D30) *Scutellaria baicalensis* Georgi | root | 12.3 | | 5 |
| (D31) *Spatholobus suberectus* Dunn | stem | 75.4 | 0 | |
| (D32) *Syzygium aromaticum* (L.) Merr. et Perry | flower bud | 98.6 | 0 | |
| (D33) *Terminalia arjuna* Wight et Arn. | bark | 100 | 0 | |
| (D34) *Terminalia belerica* Roxb. | fruit peel | 104.4 | 0 | |
| (D35) *Terminalia chebula* Retzus | fruit | 152 | | 0 |
| (D36) *Woodfordia floribunda* Salisb. | flower, leaf | 0 | 0 | |
| (D37) *Woodwardia orientalis* Sw. | rhizome | 105.4 | 0 | |
| (D38) *Zizyphus jujuba* Miller var. inermis Rehder | fruit | 74.7 | 51.8 | |

TEST EXAMPLE 4

Anti-varicella-zoster virus activity of the crude drugs shown in Table 4 (group E) was determined in the same manner as in the Test Example 1. The results obtained are shown in Table 4. The crude belonging to group E were thus proved to have anti-varicella-zoster virus activity. In the case of using *Plagiogyria matsumureana* Makino, methanol extract was used in place of water extract.

TABLE 4

Anti-varicella-zoster Virus Activity

| Species | Part | Plaque Formation Efficiency (%) 100 μg/ml | 200 μg/ml |
|---|---|---|---|
| (E1)*Alpinia officinarum* Hance | rhizome | | 0 |
| (E2)*Areca catechu* L. | seed | | 0 |
| (E3)*Artemisia princeps* Pamp. | leaf | | 46.7 |
| (E4)*Bupleurum fakatum* L. | root | 31.2 | |
| (E5)*Cassia fistula* L. | bark | | 0 |
| (E6)*Coptis chinensis* Franch. | rhizome | | 0 |
| (E7)*Cyrtomium fortunei* J. Sm. | rhizome | | 0 |
| (E8)*Drynaria fortunei* (Kunze) J. Smith | rhizome | | 0 |
| (E9)*Geranium thunbergii* Sieb. et Zucc. | whole plant | | 14.7 |
| (E10)*Glycyrrhiza uralensis* Fisher | root, stolon | 17.2 | |
| (E11)*Juglans mandshurica* Maxim. | bark | | 0 |
| (E12)*Panax ginseng* C.A. Meyer | root | 55.9 | |
| (E13)*Paeonia suffruticosa* Andrews | root bark | | 39.7 |
| (E14)*Phellodendron amurense* Ruprecht | bark | | 0 |
| (E15)*Plagiogyria matsumureana* Makino | rhizome | | 0 |
| (E16)*Polygala tenuifolia* Willd. | root | | 0 |
| (E17)*Polygonum cuspidatum* Sieb. et Zucc. | root, rhizome | | 0 |
| (E18)*Poria cocos* Wolf | hoelen | 50.5 | |
| (E19)*Punica granatum* L. | root bark, fruit peel | | 0 |
| (E20)*Quercus acutissima* Carruthers | bark | | 0 |
| (E21)*Rheum palmatum* L. | rhizome | | 0 |
| (E22)*Rhus javanica* L. | gall | | 0 |
| (E23)*Syzygium aromaticum* (L.) Merr. et Perry | flower bud | | 26.6 |
| (E24)*Terminalia arjuna* Wight et Arn. | bark | | 0 |
| (E25)*Terminalia chebula* Retzus | fruit | | 0 |
| (E26)*Woodwardia orientalis* Sw. | rhizome | | 0 |
| (E27)*Dryopteris crassirhizoma* Nakai | rhizome | | 1.6 |

TEST EXAMPLE 5

Anti-CMV activity of the crude drugs shown in Table 5 (group F) was determined in the same manner as in Test Example 1. The results obtained are shown in Table 5. From these results, the crude drugs belonging to group F were proved to have anti-CMV activity. In the case of using *Plagiogyria matsumureana* Makino, methanol extract was used in place of water extract.

Example 1, except for using Vero E6 cells and changing the concentration of the extract solution. The results obtained are shown in Table 6. It can be seen that the extract of the crude drug according to the present invention significantly reduced the efficiency of plaque formation at such a concentration as low as 300 μg/ml or less and thus exhibited antiviral activity.

Cytotoxicity of each extract solution was also determined. While some of the extract solutions tested

TABLE 5

Anti-CMV Activity

| Species | Part | Plaque Formation Efficiency (%) 100 μg/ml | 200 μg/ml |
|---|---|---|---|
| (F1)*Areca catechu* L. | seed | | 17.8 |
| (F2)*Artemisia princeps* Pamp. | leaf | | 0 |
| (F3)*Cassia fistula* L. | bark | | 0 |
| (F4)*Coptis chinensis* Franch. | rhizome | | 0 |
| (F5)*Cyrtomium fortunei* J. Sm. | rhizome | | 21.7 |
| (F6)*Drynaria fortunei* (Kunze) J. Smith | rhizome | | 0 |
| (F7)*Geranium thunbergii* Sieb. et Zucc. | whole plant | | 0 |
| (F8)*Geum japonicum* Thunb. | whole plant | | 0 |
| (F9)*Juglans mandshurica* Maxim. | bark | | 0 |
| (F10)*Machilus thunbergii* Sieb. et Zucc. | bark | | 0 |
| (F11)*Paeonia suffruticosa* Andrews | root bark | | 47.4 |
| (F12)*Phellodendron amurense* Ruprecht | bark | | 0 |
| (F13)*Plagiogyria matsumureana* Makino | rhizome | | 33.6 |
| (F14)*Polygala tenuifolia* Willd. | root | | 0 |
| (F15)*Polygonum cuspidatum* Sieb. et Zucc. | root, rhizome | | 0 |
| (F16)*Punica granatum* L. | root bark, fruit peel | | 0 |
| (F17)*Quercus acutissima* Carruthers | bark | 0 | |
| (F18)*Rheum palmatum* L. | rhizome | | 0 |
| (F19)*Rhus javanica* L. | gall | | 0 |
| (F20)*Syzygium aromaticum* (L.) Merr. et Perry | flower bud | | 0 |
| (F21)*Terminalia arjuna* Wight et Arn. | bark | | 0 |
| (F22)*Terminalia chebula* Retzus | fruit | | 0 |
| (F23)*Woodwardia orientalis* Sw. | rhizome | | 0 |

TEST EXAMPLE 6

Antiviral activity of the crude drugs shown in Table 6 below was examined in the same manner as in Test showed cytotoxicity at a concentration of 300 μg/ml, they exhibited antiviral activity at low concentrations showing no cytotoxicity.

TABLE 6

| | | Antiviral Activity (in Vero E6 Cells) | | | |
|---|---|---|---|---|---|
| | Concn. of Extract Solution | Plaque Formation Efficiency (%) | | | |
| Species (part) | (μg/ml) | Herpes I | Polio | Measles | Cytotoxicity |
| *Cassia fistula* L. (bark) | 0 | 100 | 100 | 100 | |
| | 10 | 101.4 | 101.7 | 97.5 | |
| | 50 | 92.2 | 66.9 | 95.6 | |
| | 100 | 29.5 | 37.7 | 76.5 | |
| | 300 | 0 | 2.8 | 7 | ± |
| *Terminalia arjuna* Wight et Arn. (bark) | 0 | 100 | 100 | 100 | |
| | 10 | 108.8 | 86.8 | 92.1 | |
| | 50 | 78.3 | 88.7 | 92.7 | |
| | 100 | 47 | 0 | 0 | + |
| | 300 | 0 | 0 | 0 | + |
| *Alpinia officinarum* Hance (rhizome) | 0 | 100 | 100 | 100 | |
| | 10 | 105.1 | 98.8 | 92.4 | |
| | 50 | 101.8 | 56 | 89.5 | |
| | 100 | 76.5 | 30.7 | 106.7 | |
| | 300 | 0 | 0 | 14.9 | + |
| *Juglans mandshurica* Maxim. (bark) | 0 | 100 | 100 | 100 | |
| | 10 | 96.3 | 75.1 | 91.4 | |
| | 50 | 112 | 57.2 | 89.2 | |
| | 100 | 73.6 | 24.1 | 86.3 | |
| | 300 | 0 | 4.8 | 3.5 | + |
| *Punica granatum* L. (fruit peel) | 0 | 100 | 100 | 100 | |
| | 10 | 87.9 | 45.1 | 84 | |
| | 50 | 102.1 | 25.4 | 121.8 | |
| | 100 | 83.2 | 14.6 | 102.8 | |
| | 300 | 2.9 | 5.8 | 0 | + |
| *Geranium thunbergii* Sieb. et Zucc. (whole plant) | 0 | 100 | 100 | 100 | |
| | 10 | 100.7 | 66.8 | 94.7 | |
| | 50 | 90.7 | 40.7 | 122.7 | |
| | 100 | 91.6 | 30 | 104.7 | |
| | 300 | 23.5 | 18.3 | 0 | ± |
| *Drynaria fortunei* (Kunze) J. Smith (rhizome) | 0 | 100 | 100 | 100 | |
| | 10 | 110.7 | 87.8 | 96.4 | |
| | 50 | 90.7 | 68.5 | 117.8 | |
| | 100 | 87.4 | 59 | 101.8 | |
| | 300 | 0 | 25.4 | 87.1 | + |
| *Polygonum cuspidatum* Sieb. et Zucc. (root, rhizome) | 0 | 100 | 100 | 100 | |
| | 10 | 125 | 85.4 | 73.8 | |
| | 50 | 110 | 74.6 | 107.6 | |
| | 100 | 97.1 | 36.9 | 107.1 | |
| | 300 | 0 | 0 | 0 | + |
| *Punica granatum* L. (root bark) | 0 | 100 | 100 | 100 | |
| | 10 | 93.7 | 52.4 | 104.8 | |
| | 50 | 78.7 | 9.4 | 96.7 | |
| | 100 | 79.2 | 7.4 | 45.4 | ± |
| | 300 | 0 | 0 | 0 | + |
| *Terminalia chebula* Retzus (fruit) | 0 | 100 | 100 | 100 | |
| | 10 | 89.4 | 41.8 | 103.9 | |
| | 50 | 87 | 16.8 | 112.2 | |
| | 100 | 83.6 | 18.8 | 98.8 | |
| | 300 | 0 | 4.1 | 0 | + |
| *Paeonia suffruticosa* Andrews (root bark) | 0 | 100 | 100 | 100 | |
| | 10 | 89.9 | 103.5 | 85.1 | |
| | 50 | 101.4 | 97.9 | 86 | |
| | 100 | 101.4 | 72.4 | 97.9 | |
| | 300 | 76.3 | 64.4 | 113.7 | |

TEST EXAMPLE 7

Antiherpesviral activity (anti-herpesvirus type I activity, anti-varicella-zoster virus activity, and anti-CMV activity) of the crude drugs shown in Table 7 below were examined by the plaque formation test. The antiherpesvirus type I activity test was carried out using Vero E6 cells and an extract solution diluted to 300 μg/ml except where noted; and the anti-varicella-zoster virus activity test and anti-CMV activity test were carried out by using HEL cells and an extract solution diluted to 200 μg/ml. The results obtained are shown in Table 7. As can be seen from the Table, the extract of the crude drug according to the present invention significantly reduced the efficiency of plaque formation at such a concentration as low as 500 μg/ml or less and thus exhibited antiherpesviral activity. Further, *Cyrtomium fortunei* J. Sm. exhibited similar effects in its methanol extract and aqueous extract, suggesting that a crude drug whose methanol extract exhibits antiviral activity also exhibits antiviral activity in its aqueous extract as well.

TABLE 7

Antiherpesviral Activity

| Species (part) | Plaque Formation Efficiency (%) | | |
|---|---|---|---|
| | Herpesvirus, I 300 μg/ml | Varicella-zoster Virus 200 μg/ml | CMV 200 μg/ml |
| *Cyrtomium fortunei* (Kunze) J. Smith# (rhizome) | 0 | 0 | 0 |
| *Cassia fistula* L. (bark) | 0 | 0 | 0 |
| *Areca catechu* L. (seed) | 0* | 0 | 17.8 |
| *Artemisia princeps* Pamp. (leaf) | 0* | 46.7 | 0 |
| *Terminalia arjuna* Wight et Arn. (bark) | 0 | 0 | 0 |
| *Terminalia chebula* Retzus (fruit) | 0 | 0 | 0 |
| *Punica granatum* L. (fruit peel) | 0 | 0 | 0 |
| *Punica granatum* L. (root bark) | 0* | 0 | 0 |
| *Geum japonicum* Thunb. (whole plant) | 0* | 54.9 | 0 |
| *Drynaria fortunei* (Kunze) J. Smith (rhizome) | 0 | 0 | 0 |
| *Polygonum cuspidatum* Sieb. et Zucc. (root, rhizome) | 0* | 0 | 0 |
| *Geranium thunbergii* Sieb. et Zucc. (whole plant) | 23.5 | 14.7 | 0 |
| *Alpinia officinarum* Hance (rhizome) | 0 | 0 | 73.0** |
| *Juglans mandshurica* Maxim. (bark) | 0 | 0 | 0 |
| *Coptis chinensis* Franch. (rhizome) | 0* | 0 | 0 |
| *Polygala tenuifolia* Willd. (root) | 0* | 0 | 0 |
| *Machilus thunbergii* Sieb. et Zucc. (bark) | 17.8 | 0 | 0 |
| *Rheum palmatum* L. (rhizome) | 0 | 0 | 0 |
| *Paeonia suffruticosa* Andrews (root bark) | 0* | 39.7 | 47.4 |
| *Rhus javanica* L. (gall) | 0* | 0 | 0 |
| *Phellodendron amurense* Ruprecht (bark) | 0* | 0 | 0 |
| *Syzygium aromaticum* (L.) Merr. et Perry (flower bud) | 0 | 26.6 | 0 |
| *Cyrtonium fortunei* J. Sm. (rhizome) | 0 | 0 | 21.7 |
| *Woodwardia orientalis* Sw. (rhizome) | 0 | 0 | |
| *Dryoperis crassirhizoma* Nakai (rhizome) (M) | 35.9 | 1.6 | 73** |
| *Woodwardia orientalis* Sw. (rhizome) (M) | 0 | 0 | 0 |
| *Cyrtomium fortunei* J. Sm. (rhizome) (M) | 0 | 0 | 0 |
| *Plagiogyria matsumureana* Makino (rhizome) (M) | 0 | 0 | 33.6 |

Note:
*: An extract solution having a concentration of 500 μg/ml was used.
**: The plaque size was very small.
(M): A methanol extract was used in place of an aqueous extract.

TEST EXAMPLE 8

Antiherpesviral activity of a combination of an extract solution of *Cyrtomium fortunei* (Kunze) J. Smith# (hereinafter abbreviated as *Cryt. f.#*) and an extract solution of the crude drug shown in Table 8 was determined using herpesvirus type I and Vero E6 cells. Each extract solution was diluted to 100 μg/ml in a single use, and in a combined use, two extract solutions each having a concentration of 100 μg/ml were mixed. The results obtained are shown in Table 8.

Antiherpesviral activity of a combination of *Cryt. f.#* and *Artemisia princeps* Pamp. was also determined in the same manner, except for using HEL cells, varicella-zoster virus, and CMV. The results obtained are shown in Table 9.

As is apparent from Tables 8 and 9, a combination of *Cryt. f.#* and other crude drugs showed appreciable synergism.

TABLE 8

Antiherpesviral Activity (Herpesvirus, Type I)

| Species (part) | Plaque Formation Efficiency (%) | |
|---|---|---|
| | Single Use | Combined Use |
| *Crytomium fortunei* J. Sn.# (rhizome) | 82.9 | — |
| *Cassia fistula* L. (bark) | 60 | 0 |
| *Areca catechu* L. (seed) | 65.2 | 0 |
| *Artemisia princeps* Pamp. (leaf) | 66.1 | 37.1 |
| *Terminalia arjuna* Wight et Arn. (bark) | 56.7 | 0 |
| *Terminalia chebula* Retzus (fruit) | 83.6 | 16.1 |
| *Punica granatum* L. (fruit peel) | 86.2 | 0 |
| *Punica granatum* L. (root bark) | 63.8 | 0 |
| *Geum japonicum* Thunb. (whole plant) | 98.6 | 38.7 |
| *Drynaria fortunei* (Kunze) J. Smith (rhizome) | 100.5 | 0 |
| *Polygonum cuspidatum* Sieb. et Zucc. (root, rhizome) | 118.6 | 28.4 |
| *Geranium thunbergii* Sieb. et Zucc. (whole plant) | 83.9 | 0 |
| *Alpinia officinarum* Hance (rhizome) | 91 | 44.1 |
| *Juglans mandshurica* Maxim. (bark) | 61.4 | 25.4 |
| *Coptis chinensis* Franch. (rhizome) | 92.9 | 10.3 |
| *Polygala tenuifolia* Willd. (root) | 27.1 | 0 |
| *Machilus thunbergii* Sieb. et Zucc. (bark) | 117.6 | 0 |
| *Rheum palmatum* L. (rhizome) | 76.7 | 0 |
| *Paeonia suffruticosa* Andrews (root bark) | 103.8 | 67.3 |
| *Rhus javanica* L. (gall) | 0 | 0 |
| *Phellodendron amurense* Ruprecht (bark) | 111 | 64 |

TABLE 8-continued

Antiherpesviral Activity (Herpesvirus, Type I)

| | Plaque Formation Efficiency (%) | |
|---|---|---|
| Species (part) | Single Use | Combined Use |
| *Syzygium aromaticum* (L.) Merr. et Perry (flower bud) | 102.4 | 61.7 |

TABLE 9

| | Antiviral Activity | | | |
|---|---|---|---|---|
| | Plaque Formation Efficiency (%) | | | |
| | Varicella Virus | | CMV | |
| Species (part) | Single Use | Combined Use | Single Use | Combined Use |
| *Cyrtomium fortunei* J. Sm.# (rhizome) | 7 | — | 49 | — |
| *Artemisia princeps* Pamp. (leaf) | 48.4 | 0 | 56.9 | 0 |

TEST EXAMPLE 9

Because the crude drugs according to the present invention are usually administered orally, the components which are absorbed through the gastrointestinal tract appear to be effective. Accordingly, the antiherpesviral activity of the serum prepared from the blood of a guinea pig having orally or intragastrointestinally received an extract solution of *Cryt. f.#* was determined according to the following animal test method.

For comparison, the antiherpesviral activity of the serum prepared in the same manner, except for replacing the *Cryt. f.#* extract with acyclovir ("Zovirax 200" sold by Wellcome Co.) (hereinafter abbreviated as Acv) known as an antiviral agent, was also determined. Acv tablets were ground to powder in a mortar and suspended in water or a crude drug extract solution in a prescribed concentration.

Animal Test Method:

Laparotomy was performed on a Hartley female guinea pig (body weight: 300–350 g) under etherization. Into each of the stomach, the small intestine, and the large intestine was infused 10 ml of water, an Acv suspension, a *Cryt. f.#* extract solution, or a mixed solution of Acv and the extract solution, and the abdomen was immediately closed. Two hours from the operation, blood was taken from the heart. The serum separated from the blood was inactivated by heating at 56° for 30 minutes.

Vero cells was monolayer-cultured in a 25 cm²-volume plastic flask and infected with 0.01 PFU/ml of herpesvirus. After adsorption for 1 hour, the infected cells were cultured in MEM containing 30 to 40% of the above-prepared inactivated serum. After cultivation for a given time (1 to 4 days), the cells were destroyed by freezing and thawing three times, followed by centrifugation. The amount of the virus in the supernatant liquor was measured by the plaque formation test using Vero cells. The results obtained are shown in Tables 10 and 11.

As is apparent from the results in Tables 10 and 11, antiherpesviral activity was displayed in both the *Cryt. f.#* group and the Acv group, and the combined use of *Cryt. f.#* and Acv showed significant synergism.

TABLE 10

| | | Amount of Virus (PFU/ml) | | | |
|---|---|---|---|---|---|
| Run No. | Sample No. | Normal Serum | Serum of Cryt. f.# Group | Serum of Acv Group | Serum of Cryt. f.# + Acv Group |
| 1 | a | $2.05 \times 10^8$ | $2.15 \times 10^8$ | $2.58 \times 10^7$ | $1.17 \times 10^7$ |
| | b | $2.33 \times 10^8$ | $2.18 \times 10^8$ | $5.83 \times 10^7$ | $1.64 \times 10^7$ |
| | c | $2.35 \times 10^8$ | $1.98 \times 10^8$ | $6.85 \times 10^7$ | $1.97 \times 10^7$ |
| | mean ± σ* | $(2.24 \pm 0.17) \times 10^8$ | $(2.10 \pm 0.11) \times 10^8$ (p = 0.29)** | $(5.09 \pm 2.20) \times 10^7$ | $(1.59 \pm 0.40) \times 10^7$ (p = 0.056)*** |
| 2 | a | $3.25 \times 10^8$ | $1.80 \times 10^8$ | $1.68 \times 10^7$ | $8.30 \times 10^5$ |
| | b | $2.30 \times 10^8$ | $1.83 \times 10^8$ | $1.54 \times 10^7$ | $4.88 \times 10^5$ |
| | c | — | $1.58 \times 10^8$ | — | $2.17 \times 10^6$ |
| | mean ± σ | $2.78 \times 10^8$ | $(1.74 \pm 0.14) \times 10^8$ (p = 0.067)** | $1.61 \times 10^7$ | $(1.33 \pm 1.30) \times 10^6$ (p < 0.01)*** |
| 3 | a | $1.55 \times 10^8$ | $1.10 \times 10^8$ | $7.67 \times 10^5$ | $1.75 \times 10^5$ |
| | b | $1.20 \times 10^8$ | $1.93 \times 10^8$ | $1.25 \times 10^6$ | $5.00 \times 10^4$ |
| | c | $1.63 \times 10^8$ | $2.75 \times 10^7$ | $1.02 \times 10^6$ | $2.50 \times 10^4$ |
| | mean ± σ | $(1.46 \pm 0.23) \times 10^8$ | $(1.10 \pm 0.83) \times 10^8$ (p = 0.51)** | $(5.09 \pm 2.20) \times 10^6$ | $(8.33 \pm 8.04) \times 10^4$ (p < 0.01)*** |
| 4 | a | $1.73 \times 10^8$ | $3.50 \times 10^7$ | $4.67 \times 10^6$ | $3.67 \times 10^5$ |
| | b | $1.80 \times 10^8$ | $1.05 \times 10^8$ | $2.65 \times 10^6$ | $1.37 \times 10^6$ |
| | c | $2.03 \times 10^8$ | $1.50 \times 10^8$ | $6.00 \times 10^6$ | $9.00 \times 10^5$ |
| | mean ± σ | $(1.85 \pm 0.16) \times 10^8$ | $(9.67 \pm 5.80) \times 10^7$ (p = 0.063)** | $(4.44 \pm 1.68) \times 10^6$ | $(8.79 \pm 5.00) \times 10^5$ (p = 0.025)*** |

Note:
*: Standard deviation (hereinafter the same)
**: t-Test value with respect to the normal serum.
***: t-test value with respect to the serum of the Acv group.

TABLE 11

| Run No. | Sample No. | Normal Serum | Serum of Cryt. f.# (20 mg/ml) Group | Serum of Acv (200 mg/ml) Group | Serum of Cryt. f.# + Acv Group | | |
|---|---|---|---|---|---|---|---|
| | | | | | 1 mg/ml of Cryt. f.# | 5 mg/ml of Cryt. f.# | 20 mg/ml of Cryt. f.# |
| 1 | a | $3.30 \times 10^8$ | $1.30 \times 10^8$ | $4.93 \times 10^7$ | $8.25 \times 10^6$ | $2.50 \times 10^5$ | $2.00 \times 10^{16}$ |
| | b | $3.03 \times 10^8$ | $1.45 \times 10^8$ | $3.80 \times 10^7$ | $1.58 \times 10^7$ | $6.25 \times 10^6$ | $2.00 \times 10^6$ |
| | c | $2.75 \times 10^8$ | $2.08 \times 10^8$ | $7.83 \times 10^7$ | $8.25 \times 10^6$ | $2.50 \times 10^5$ | $1.00 \times 10^6$ |
| | mean ± σ | $(3.03 \pm 0.28) \times 10^8$ | $(1.61 \pm 0.41) \times 10^7$ $(p < 0.01)^*$ | $(5.52 \pm 2.08) \times 10^7$ | $(1.59 \pm 0.40) \times 10^7$ $(p < 0.05)^{}$ | $(2.25 \pm 3.46) \times 10^6$ $(p < 00.05)^{}$ | $(1.67 \pm 0.58) \times 10^6$ $(p < 0.05)^{**}$ |

Amount of Virus (PFU/ml)

Note:
*: t-Test value with respect to the normal serum.
**: t-Test value with respect to the serum of the Acv group.

TEST EXAMPLE 10

Since the antiherpesviral activity of Acv is known, whether or not the synergism shown in Test Example 9 had been attributed to the improvement of Acv absorption by the extract solution of Cryt. f.# was examined by measuring Acv concentration in blood when Acv was administered alone or in combination with a Cryt. f.# extract solution.

An Acv suspension or a mixture of Acv and an extract solution of Cryt. f.# was orally or intragastrointestinally administered to a guinea pig. One hour from the administration, blood was taken from the heart, and an inactivated serum was prepared therefrom in the same manner as in Test Example 9.

To a 100 μl aliquot of the serum were added 100 μl of acetonitrile and 20 μl of a 100 mM sodium acetate solution, and the mixture was centrifuged (10000 rpm × 10 mins.). The supernatant liquor (150 μl) was evaporated to dryness in an evaporator, and the residue was dissolved in 25 μl of a solvent for reverse phase liquid chromatography which contained 16.7 mM of adenine as an internal standard to prepare a sample solution.

The sample solution was separated into Acv and adenine by reverse phase liquid chromatography in a usual manner. Each peak area was measured with an automatic integrator, and the Acv content was obtained from the previously prepared calibration curve. The results obtained are shown in Table 12. From the results in Table 12, it is not recognized that the Acv absorption was accelerated by the combined use of the Cryt. f.# extract solution. It is therefore considered that a Cryt. f.# extract solution per se possesses antiherpesviral activity in its absorbable fraction.

Further, 0.5 ml of an Acv preparation or 0.5 ml of a mixture of Acv and a varied concentration of Cryt. f.# extract solution was orally administered to a 6-week-old DDY male mouse, and the Acv concentration in blood was measured in the same manner as described above. The results obtained are shown in Table 13. As is apparent from Table 13, no increase in Acv concentration in blood was observed in the group having received Acv combined with Cryt. f.#. Accordingly, the Cryt. f.# extract solution is believed to have antiherpesviral activity by itself.

Antiherpesviral activity was examined in combined use of Acv and an extract solution of the crude drug shown in Table 14.

As is apparent from the results in Table 14, antiherpesviral activity was displayed in the combined use of Acv and an extract solution of the crude drug showed significant synergism.

TABLE 12

Acv Concentration in Guinea Pig Blood

| Serum Sample No. | Acv Concentration in Blood (μM) | | | |
|---|---|---|---|---|
| | Acv (200 mg) Group | Acv (200 mg) + Cryt. f.# Group | | |
| | | 1 mg/ml of Cryt. f.# | 5 mg/ml of Cryt. f.# | 20 mg/ml of Cryt. f.# |
| 1 | 21.6 | 76.4 | 92.9 | 152.7 |
| 2 | 185.1 | 129.6 | 103 | 21.6 |
| 3 | 59.1 | 72.7 | 69.1 | 42.5 |
| Mean ± σ | 88.6 ± 85.6 | 92.9 ± 31.9 | 88.3 ± 17.4 | 72.2 ± 70.4 |

TABLE 13

Acv Level in Mouse Blood (p.o.)

| Serum Sample No. | Acv Blood Level (μM) | | | |
|---|---|---|---|---|
| | Acv (10 mg/kg) Group | Acv (100 mg/kg) + Cryt. f.# Group | | |
| | | 2 mg/ml of Cryt. f.# | 10 mg/ml of Cryt. f.# | 20 mg/ml of Cryt. f.# |
| 1 | 3.2 | 1.7 | 2.3 | 0.4 |
| 2 | 1.7 | 1.4 | 1.1 | 4 |
| 3 | 0.5 | 1.6 | 3.5 | 3.2 |
| 4 | 5.1 | 2.5 | 1.6 | 0.5 |
| 5 | 0.8 | 4.7 | 1.9 | 4.1 |
| 6 | 1.9 | 2.9 | 2.6 | 2 |
| 7 | 1.9 | 2 | 1.5 | 3.3 |
| 8 | 1.7 | 2.4 | 5.2 | 4 |
| 9 | 2.9 | 9.5 | — | 1.6 |
| 10 | 4 | 2.3 | — | 4.4 |
| 11 | — | — | — | 1 |
| Mean ± σ | 2.28 ± 1.49 | 3.10 ± 2.43 | 2.46 ± 1.33 | 2.59 ± 1.53 |

TABLE 14

Antiherpesviral activity in combination use of Acv and hot water extract of crude drug

| Species | Concn. of Extract solution (μg/ml) | Plaque Formation Efficiency (%) | |
|---|---|---|---|
| | | Acv | Acv + Crude drug / Crude drug |
| Acyclovir | 0.35 | 53.6 | |
| Alpinia officinarum Hance | 200 | 58 | 30.6 |
| Caesalpinia sappan L. | 40 | 53.3 | 0.2 |
| Geum japonicum Thunb. | 120 | 52.8 | 1.1 |
| Paeonia suffruticosa Andrews | 400 | 59.5 | 26 |
| Phellodendron amurense Ruprecht | 400 | 61.5 | 24.5 |
| Polygala tenuifolia Willd. | 400 | 55.2 | 15.7 |

TABLE 14-continued

Antiherpesviral activity in
combination use of Acv and hot water extract of crude drug

| Species | Concn. of Extract solution (μg/ml) | Plaque Formation Efficiency (%) | | |
|---|---|---|---|---|
| | | Acv | Crude drug | Acv + Crude drug |
| *Polygonum cuspidatum* Sieb. et Zucc | 200 | | 59.4 | 20.6 |
| *Punica granatum* L. | 50 | | 50.9 | 1 |
| *Syzygium aromaticum* (L.) Merr. et Perry | 60 | | 61.2 | 0.2 |
| *Terminalia arjuna* Wight et Arn. | 50 | | 52.8 | 24.8 |

TEXT EXAMPLE 11

Antiherpesviral activity of various crude drugs shown in Table 15 below in guinea pigs (p.o.) was determined as follows.

A control group of guinea pigs was allowed to take water freely for 5 days. A 5 mg/ml extract solution of Cryt. F.' was given to another group freely by mouth for 5 days. Still another group was allowed to take a 5 mg/ml solution of *Areca catechu* L. freely for 5 days. Other groups were orally given 10 ml of a 20 mg/ml solution of each of the other crude drug extracts. Blood was taken from each animal, and an inactivated serum was prepared therefrom in the same manner as in Test Example 9. A plaque formation test was conducted using the resulting serum sample. The results obtained are shown in Table 15. It is obvious from the results that each crude drug extract exhibited antiherpesviral activity.

TABLE 15

| Crude Drug | Plaque Formation Efficiency (%) |
|---|---|
| Water (control) | 100.0 |
| Acyclovir (6.7 mg/ml) | 18.2 |
| (B2)*Alpinia officinarum* Hance | 6.8 |
| (B5)*Areca catechu* L. | 57.3 |
| (B17)*Crytomium fortunei* J. Sm.# | 45.5 |
| (B8)*Brucea javanica* (L.) Merr. | 20.4 |
| (B9)*Caesalpinia sappan* L. | 43.4 |
| (B11)*Cassia fistula* L. | 45.0 |
| (B14)*Cinnamomum sintok* Blume | 41.9 |
| (B18)*Drynaria fortunei* (Kunze) J. Smith | 34.0 |
| (B20)*Elaeocarpus grandiflorus* Smith | 15.4 |
| (B24)*Geranium thunbergii* Sieb. et Zucc. | 50.0 |
| (B25)*Geum japonicum* Thunb. | 22.5 |
| (B28)*Juglans mandshurica* Maxim. | 12.6 |
| (B30)*Paeonia suffruticosa* Andrews | 61.4 |
| (B32)*Phellodendron amurense* Ruprecht | 30.4 |
| (B34)*Polygala tenuifolia* Willd. | 8.3 |
| (B35)*Polygonum cuspidatum* Sieb. at Zucc. | 65.6 |
| (B36)*Prunella vulgaris* L. subsp. asiatica Hara | 58.5 |
| (B37)*Punica granatum* L. (root bark and fruit peel) | 54.3 |
| (B40)*Rhus javanica* L. | 87.3 |
| (B46)*Terminalia arjuna* Wight et Arn. | 39.0 |
| (B47)*Terminalia belerica* Roxb. | 31.2 |
| (B48)*Terminalia chebula* Retzus | 87.4 |
| (B50)*Woodfordia floribunda* Salisb. | 80.1 |
| (B51)*Woodwardia orientalis* Sw. | 82.1 |
| *Syzygium aromaticum* (L.) Merr. et Perry | 50.5 |

TEST EXAMPLE 12

Mouse was infected with Herpes simplex virus at the right midflank to examine the antiviral activity of the crude drug by a rate of herpes zoster formation and a rate of death.

In vivo antiviral activity of *Geum japonicum* Thunb. or *Juglans mandshurica* Maxim. in mice infected with herpes simplex virus was examined as follows.

The hair on the side abdomen of 6 to 7-week-old male BALB/C mice was removed by a chemical hair remover (produced by Shiseido Co., Ltd.). The hairless skin was scratched at random ten times with an intradermal injection needle 26G, and 10 μl of a herpes simplex virus I (Hayashida strain) (having been proliferated in Vero E6 cells) suspension ($10^6$ PFU) was applied to the scarified area.

Immediately after the infection, 0.5 ml of the crude drug extract solution having a concentration of from 2 to 20 mg/ml (corresponding to 10 mg-drug/mouse) was orally given to the animal every 8 hours (3 times/day) for at least consecutive 10 days. A control group was orally given the equal volumes of water The development of skin lesions and mortality were monitored three times a day and any change observed on the infected skin was scored on the following basis. The results obtained are shown in Table 16.

| Score Standard: | |
|---|---|
| 0 ... | No lesion |
| 2 ... | Vesicles in local region (bulla and erosion) |
| 6 ... | Mild zosteriform lesion |
| 8 ... | Moderate zosteriform lesion |
| 10 ... | Severe zosteriform lesion |
| Death | |

As is apparent from Table 16, the group having orally received the extract solution exhibited a reduced rate of death, an increased survival rate and a reduced rate of herpes zoster formation as compared with the control group, proving the antiherpesviral activity of the crude drug in vivo.

TABLE 16

| Crude Drug | Rate of Herpes Zoster Formation | Death Rate | Average Survival Days |
|---|---|---|---|
| Water (control) | 6/6 (100%) | 6/6 (100%) | 8.2 ± 0.4 |
| *Geum japonicum* Thunb. | 3/4 (75%) | 3/4 (75%) | 10.2 ± 1.8* |
| *Juglans mandshurica* Maxim. | 2/3 (67%) | 2/3 (67%) | 10.0 ± 2.7 |

Note:
*significance level $p < 0.05$

As described in the foregoing test examples, antiherpesviral activity of the crude drugs belonging to group A according to the present invention can be ascertained by the above-described in vitro screening test. Further, the serum prepared from the guinea pig having orally or intragastrointestinally received the extract of the crude drug of group B exhibited antiherpesviral activity. Furthermore, the crude drug extract having antiherpesviral activity obviously inhibited herpesvirus growth in mice (p.o.) (cf. Table 16). The results coincided with the results shown in Table 1 which was conducted in vitro.

From all these test results, it was thus revealed that a crude drug of group B which exhibits antiherpesviral activity in vitro also exhibits the same activity in vivo.

TEST EXAMPLE 13

Antipolioviral activity of *Punica granatum* L. (fruit peel) was determined by using the guinea pig serum

TEST EXAMPLE 14

Antipolioviral activity of the crude drugs shown in Table 18 below in guinea pigs (p.o.) was determined in the same manner as in Text Example 11 as follows.

A group of guinea pigs was allowed to take water or a 5 mg/ml extract solution freely for 5 days. A serum sample was prepared in the same manner as in Test Example 9 and subjected to the plaque formation test. The results obtained are shown in Table 18. It is obvious from the results that each crude drug extract exhibited antipolioviral activity.

TABLE 18

| | | Amount of Virus (PFU/ml) | | | |
|---|---|---|---|---|---|
| Run No. | Sample No. | Normal Serum | Serum of Term. c.[1] Group | Serum of Pun. g.[2] Group | Serum of Are. c.[3] Group |
| 1 | a | $5.53 \times 10^5$ | $5.42 \times 10^5$ | $2.70 \times 10^5$ | — |
|  | b | $4.90 \times 10^5$ | $2.78 \times 10^5$ | $2.48 \times 10^5$ | — |
|  | c | $5.65 \times 10^5$ | $5.13 \times 10^5$ | $4.25 \times 10^5$ | — |
|  | Mean ± σ | $(5.36 \pm 0.40) \times 10^5$ | $(4.44 \pm 1.45) \times 10^5$ $(p < 0.5)^*$ | $(3.14 \pm 0.965) \times 10^5$ $(p < 0.05)^*$ |  |
|  |  | 100% | 85.10%** | 60.20%** |  |
| 2 | a | $1.18 \times 10^7$ | $6.83 \times 10^6$ | $7.50 \times 10^6$ | $7.00 \times 10^6$ |
|  | b | $1.02 \times 10^7$ | $1.07 \times 10^7$ | $9.17 \times 10^6$ | $7.33 \times 10^6$ |
|  | c | $1.22 \times 10^7$ | — | $9.12 \times 10^6$ | — |
|  | Mean ± σ | $(1.14 \pm 0.11) \times 10^7$ | $8.77 \times 10^6$ | $(8.61 \pm 0.96) \times 10^6$ $(p < 0.05)^*$ | $7.17 \times 10^6$ |
|  |  | 100% | 76.90%** | 75.50%** | 62.90%** |

Note:
[1]*Terminalia chebula* Retzus
[2]*Punica granatum* L. (fruit peel)
[3]*Areca catechu* L.
*: t-Test value with respect to the normal serum
**: Plaque formation efficiency (percent virus growth inhibition)

prepared in the same manner as in Text Example 9. The results obtained are shown in Table 17. The results clearly demonstrate the antipolioviral activity of the serum of the *Punica granatum* group.

TABLE 17

| | Amount of Virus (PFU/ml) | | |
|---|---|---|---|
| Sample No. | Normal Serum | Serum of *Punica granatum* Group | |
|  |  | 5 mg/ml | 20 mg/ml |
| a | $9.0 \times 10^6$ | $9.5 \times 10^6$ | $7.25 \times 10^6$ |
| b | $9.0 \times 10^6$ | $8.5 \times 10^6$ | $4.75 \times 10^6$ |
| c | $1.48 \times 10^7$ | $8.25 \times 10^6$ | $6.25 \times 10^5$ |
| d | $1.05 \times 10^7$ | — | $8.25 \times 10^6$ |
| e | — | — | $5.75 \times 10^6$ |
| Mean ± σ | $(1.08 \pm 0.274) \times 10^7$ | $(8.75 \pm 0.661) \times 10^6$ $(p = 0.265)^*$ | $(6.45 \pm 1.35) \times 10^6$ $(p = 0.016)^*$ |

Note:
*: t-Test value with respect to the normal serum.

Only the fruit peel of *Punica grantum* L. was used in this Example. The fruit peel of *Punica grantum* L. showed the same effect as the root bark thereof in the present invention. *Punia grantum* which can be obtained on the market is properly a mixture of the fruit peel and the root bark in this field.

As described above, the antipolioviral activity of various crude drugs belonging to group C can be examined by in vitro screening (Test Example 2). The crude drugs of group C exhibited antipolioviral activity in the serum prepared from the guinea pig having orally or intragastrointestinally received the extract of the drug (Test Examples 13 and 14).

From these test results, it was thus revealed that a crude drug which exhibits antipolioviral activity in vitro also exhibits the same activity in vivo.

The dosage, administration route, etc. of the crude drugs included under group C are well known, and the known dose levels produce no or slight side effects. Accordingly, these crude drugs were proved effective to inhibit poliovirus growth in oral administration or intragastrointestinal administration.

TEST EXAMPLE 15

The crude drugs exhibiting antiviral activity against both DNA viruses and RNA viruses, i.e., the crude drugs of group G, are shown in Table 19 together with their data.

The crude drugs of group G were proved to exhibit antiviral activity against not only any species belonging to the familiy Herpesviridae but RNA viruses of different familiies (measles virus and poliovirus) and are therefore effective in the prevention and treatment of diseases caused by DNA viruses or RNA viruses.

TABLE 19

| | Plaque Formation Efficiency (%) | | | | | | | | |
|---|---|---|---|---|---|---|---|---|---|
| | DNA Virus | | | RNA Virus | | | | | |
| | Herpesvirus | | | Measles Virus | | | Poliovirus | | |
| | Concentration of Extract Solution (μg/ml) | | | | | | | | |
| Crude Drug (part) | 100 | 300 | 500 | 100 | 300 | 500 | 100 | 300 | 500 |
| (G1)*Areca catechu* L. (seed) | 0 |  | 0 |  | 93.6 |  | 0 | 86.5 | 0 |

TABLE 19-continued

| | Plaque Formation Efficiency (%) | | | | | | | | |
|---|---|---|---|---|---|---|---|---|---|
| | DNA Virus | | | RNA Virus | | | | | |
| | Herpesvirus | | | Measles Virus | | | Poliovirus | | |
| | Concentration of Extract Solution (μg/ml) | | | | | | | | |
| Crude Drug (part) | 100 | 300 | 500 | 100 | 300 | 500 | 100 | 300 | 500 |
| (G2)*Artemisia pinceps* Pamp. (leaf) | 65 | | 0 | 10.8 | | 13.6 | 84.3 | | 40.5 |
| (G3)*Brainia insignis* (Hook.) (J. Sm.(rhizome) | 62.7 | 0 | | 109.7 | 5.1 | | 61 | 54.6 | |
| (G4)*Brucea javanica* (L.) Merr. (seed) | 6.3 | 0 | | 37.2 | 0 | | 0 | 0 | |
| (G5)*Caesalpinia sappan* L. (bark) | 0 | 0 | | 0 | 0 | | 0 | 0 | |
| (B6)*Cassia fistula* L. (bark) | 67 | 0 | | 100 | 14.1 | | 52.1 | 2.8 | |
| (G7)*Cinnamomum sintok* Blume (bark) | 0 | 0 | | 153 | 0 | | 102.5 | 0 | |
| (G8)*Coptis chinensis* Franch. (rhizome) | 74.1 | | 0 | 5.6 | | 0 | 89.7 | | 0 |
| (G9)*Cyrtomium fortunei* J. Sm. (rhizome) | 59.6 | 0 | | 112.1 | 0 | | 66.5 | 0 | |
| (G10)*Elaeocarpus grandiflorus* Smith (fruit) | 0 | 0 | | 0 | 0 | | 0 | 0 | |
| (G11)*Foeniculum vulgare* Mill. (fruit) | 67.5 | 47.5 | | 99.3 | 47.5 | | 31.3 | 28.1 | |
| (G12)*Geranium thunbergii* Sieb. et Zucc (whole plant) | 91.6 | 23.5 | | 104.7 | 0 | | 30 | 21.4 | |
| (G13)*Juglans mandshurica* Maxim. (bark) | 73.6 | 0 | | 96.5 | 3.5 | | 35.5 | 4.8 | |
| (G14)*Paeonia suffruticosa* Andrews (root bark) | 96.5 | | 0 | 119.1 | | 0 | 124.2 | | 35.5 |
| (G15)*Phellodendron amurense* Ruprecht (bark) | 85.3 | | 29.4 | 17.2 | | 0.6 | | 103.4 | 43.3 |
| (G16)*Plagiogyria matsumureana* Makino (rhizome) | 76.1 | 50.7 | | 90.8 | 84.6 | | 73.9 | 0 | |
| (G17)*Polygala tenuifolia* Willd. (root) | 118.6 | | 0 | 100 | | 0 | 86.4 | | 0 |
| (G18)*Punica granatum* L. (root bark, fruit peel) | 0 | 0 | 0 | 0 | | 0 | 79.5 | | 0 |
| (G19)*Quercus acutissima* Carruthers (bark) | 38.2 | 9.8 | | 83.3 | 38.5 | | 98.4 | 35.6 | |
| (G20)*Rheum palmatum* L. (rhizome) | 93.2 | 0 | | 108.1 | 0 | | 13.7 | 0 | |
| (G21)*Rhus javanica* L. (gall) | 0 | | 0 | 3.4 | | 0 | 65.1 | | 4.3 |
| (G22)*Spatholobus suberectus* Dunn (stem) | 92.2 | 0 | | 75.4 | 0 | | 80.2 | 0 | |
| (G23)*Syzygium aromaticum* (L.) Merr. et Perry (flower bud) | 79.4 | 0 | | | 98.6 | | 0 | | 55.0 |
| (G24)*Terminalia arjuna* Wight et Arn. (bark) | 56.3 | 0 | | 100 | 0 | | 22.5 | 0 | |
| (G25)*Terminalia belerica* Roxb. (fruit peel) | 70.8 | 0 | | 104.4 | 0 | | 7.4 | 0 | |
| (G26)*Terminalia chebula* Retzus (fruit) | 99.6 | | 0 | 152 | | 0 | 32.6 | 0.7 | |
| (G27)*Woodfordia floribunda* Salisb. (flower, leaf) | 0 | 0 | | 0 | 0 | | 0 | 0 | |
| (G28)*Woodwardia orientalis* Sw. (rhizome) | 51.6 | 0 | | 105.4 | 0 | | 30.5 | 0 | |

The crude drugs in accordance with the present invention exhibit antiviral activity and inhibit virus growth. Therefore, appropriate use of these crude drugs brings about improved effects in the prevention and treatment of virus infectious diseases.

While, in the foregoing test examples, the crude drugs of the present invention were used in the form of an aqueous extract or a methanol extract, extracts with other alcohols, e.g., ethyl alcohol, or a water/alcohol mixed solvent may also be used. A decoction or infusion prepared by decocting the crude drug with boiling water followed by filtration through a strainer, etc. can also be used. Further, a powder preparation prepared by grinding the crude drug is also usable.

While the invention has been described in detail and with reference to specific examples thereof, it will be apparent to one skilled in the art that various changes and modifications can be made therein without departing from the spirit and scope thereof.

What is claimed is:

1. A method for treating herps virus infection, comprising orally administering to a subject in need thereof a therapeutically effective amount of an antiherpesviral agent containing at least one crude drug selected from the group consisting of the whole plant or *Ainsliaea fragrans* Champ., the rhizome of *Alpinia officinarum* Hance, the bark of *Alyxia stellata* Roem., the root of *Andropogon zizaniodes* (L.) Urban, the seed of *Areca catechu* L., the leaf of *Artemisia princeps* Pamp., the rhizome of *Brainia insignis* (Hook.) J. Sm., the seed of *Brucea javanica* (L.) Merr., the bark of *Caesalpinia sappan* L., the leaf of *Camellia japonica* L., the bark of *Cassia fistula* L., the whole plant of *Chamaesyce hyssopifolia*, the bark and branch of *Cinnamomum cassia* Blume, the bark of *Cinnamomum sintok* Blume, the rhizome of Coptis chinensis Franch., the leaf of *Cordia spinescens*, the rhizome of *Cyrtomium fortunei* J. Sm., the rhizome of *Drynaria fortunei* (Kunze) J. Smith, the rhizome of *Dryopteris crassirhizoma* Nakai, the fruit of *Elaeocarpus grandiforus* Smith, the leaf of *Epimedium koreanum* Nakai, the leaf of *Erythroxylum lucidum*, the trunk of *Erythroxylum citrifolium*, the fruit of *Foeniculum vulgare* Mill., the whole plant of *Geranium thunbergii* Sieb. et Zucc., the whole plant of *Geum japonicum* Thunb., the leaf of *Hamelia xillaris* Swartz, the branch and leaf of *Jatropha curcas* L., the bark of *Juglans madnshurica* Maxim., the bark of *Machilus thunbergii* Sieb. et Zucc., the root bark of *Paeonia suffruticosa* Andrews, the leaf of *Perilla frutescens* Britton var. acuta Kudo, the bark of *Phellodendron amurense* Ruprecht, the rhizome of *Plagiogyria matsumureana* Makino, the root of *Polygala tenuifolia* Willd., the root and rhizome of *Polygonum cuspidatum* Sieb. et Zucc., the spike of *Prunella vulgaris* L. subsp. asiatica Hara, the root bark and fruit peel of *Punica granatum* L., the bark of *Ouercus acutissima* Carruthers, the rhizome of *Rheum palmatum* L., the gall of *Rhus javanica* L., the root of *Salvia miltiorrhiza* Bunge, the leaf of *Sarcandra glabra* (Thunb.) Nakai, the flores of *Schizonepeta tenuifolia* Briquet, the whole plant of *Serjania mexicana*, the stem of *Spatholobus suberectus* Dunn, the bark of *Terminalia belerica* Roxb., the fruit of *Terminalia chebula* Retzus, the branch and leaf of *Waltheria indica* L., the flower and leaf of *Woodfordia floribunda* Salisb., the rhizome of *Woodwardia orientalis* Sw., and the fruit peel of *Zanthoxylum bungeanum* Maxim.

2. A method for treating polio virus infection, comprising orally administering to a subject in need thereof a therapeutically effective amount of an antipolioviral agent containing at least one crude drug selected from the group consisting of the rhizome of *Alpinia officinarum* Hance, the bark of *Andrographis paniculate* Nees, the root of *Andropogon zizaniodes* (L.) Urban, the rhizome of *Anemarrhena asphodeloides* Bunge, the leaf of *Arctostaphylos uva-ursi* (L.) Sprengel, the seed of *Areca catechu* L., the leaf of *Artemisia princeps* Pamp., the whole plant of *Asiasarum heterotropoides* F. Maekawa var. mandshuricum F. Maekawa, the rhizome of *Belamcanda chinesis* DC., the rhizome of *Brainia insignis* (Hook.) J. Sm., the seed of *Brucea javanica* (L.) Merr, the bark of *Caesalpinia sappan* L., the bark of *Cassia fistula* L., the bark *Cinnamomum sintok* Blume, the rhizome of *Coptis chinensis* Franch., the fruit of *Cornus officinalis* Sieb. et Zucc., the tuber of *Corydalis hurtschariznorii* Besser forma yanhusuo Y.H. Chou et C.C. Hsu, the fruit of *Curculigo orchioides* Gaertn., the rhizome of *Curcuma aeroginosa* Roxb., the rhizome of *Curcuma xanthorrhiza* Roxb., the rhizome of *Cyrtomium fortunei* J. Sm., the rhizome of *Dryopteris crassirhizoma* Nakai, the fruit of *Elaeocarpus grandiflorus* Smith, the leaf of *Elephantopus scaber* L., the fruit of *Evodia rutaecarpa* Hook. f. et Thoms., the fruit of *Foeniculum vulgare* Mill., the fruit of *forsythia suspensa* Vahl., the whole plant of *Geranium thunbergii* Sieb. et Zucc., the whole plant of *Geum japonicum* Thunb., the bark of *Juglans mandshurica* Maxim., the root of *Lithospermum erythrorhizon* Sieb. et Zucc., the aerial part of *Loranthus parasiticus* (L.) Merr., the bark of *Machilus thunbergii* Sieb. et Zucc., the rhizome of *Matteuccia struthiopteris* (L.) Todaro, the whole insect of *Mylabris sidae* Fabr., the root bark of *Paeonia suffruticosa* Andrews, the bark of *Parameria laevigata* Moldenke, the bark of *Phellodendron amurense* Ruprecht, the aerial part of *Physalis angulata* L., the rhizome of *Plagiogyria matsumureana* Makino, the root of *Polyqala tenuifolia* Wilid., the root and rhizome of *Polygonum cuspidatum* Sieb. et Zucc., the bark of *Prunus jamasakura* Siebold, the fruit of *Prunus mume* Sieb. et Zucc., the root bark and fruit peel of *Punica granatum* L., the bark of *Quercus acutissima* Carruthers, the leaf of *Quercus salicina* Blume, the fruit of *Quisqualis indica* L., the rhizome of *Rheum palmatum* L., the gall of *Rhus javanica* L., the root of *Scutellaria baicalensis* Georgi, the flower bud of *Sophora japonica* L., the root of *Sophora subprestrata* Chun et T. Chen, the stem of *Spatholobus suberectus* Dunn, the rhizome of *Struthiopteris niponica* (Kunze) Nakai, the seed of *Strychnos nux-vomica* L., the flower bud of *Syzygium aromaticum* (L.) Merr. et Perry, the bark of *Terminalia arluna* Wight et Arn., the fruit peel of *Terminalia belerica* Roxb., the fruit of *Terminalia chebula*Retzus, the leaf and branch of *Uncaria gambir* Roxb., the whole plant of *Usnea misaminensis* Vain., the flower and leaf of Woodfordia floribunda Salisb., the rhizome of *Woodwardia orientalis* Sw., and the fruit peel of *Zanthoxylum bungeanum* Maxim.

3. A method for treating measles virus infection, comprising orally administering to a subject in need thereof a therapeutically effective amount of an anti-measles virus agent containing at least one crude drug selected from the group consisting of the seed of *Areca catechu* L., the leaf of *Artemisia princeps* Pamp., the rhizome of *Belamcanda chinensis* (L.) DC., the rhizome of *Brainia insignis* (Hook.) J. Sm., the seed of *Brucea javanica* (L.) Merr, the bark of *Caesalpinia sappan* L., the bark of *Cassia fistula* L., the bark of *Cinnamomum sintok* Blume, the rhizome of *Cnidium officinale* Makino, the rhizome of *Coptis chinensis* Franch., the rhizome of *Cyrtomium fortunei* J. Sm., the fruit of *Elaeocarpus grandiflorus* Smith, the leaf of *Elephantopus scaber* L., the fruit of *Foeniculum vulgare* Mill, the fruit of *Forsythia suspensa* Vahl., the whole plant of *Geranium thunbergii* Sieb. et Zucc., the root and stolon of *Glycyrrhiza uralensis* Fisher, the bark of *Juglans mandshurica* Maxim., the bark of *Magnolia officinalis* Rehd. et Wils., the whole insect of *Mylabris sidae* Fabr., the root bark of *Paeonia suffruticosa* Andrews, the bark of *Phellodendron amurense* Ruprecht, the rhizome of *Plagiogyria matsumureana* Makino, the root of *Platycodon grandiflorum* (Jacquin) A. DC., the root of *Polygala tenuifolia* Willd., the root bark and fruit peel of *Punica granatum* L., the bark of *Quercus acutissima* Carruthers, the rhizome of *Rheum palmatum* L., the gall of *Rhus javanica* L., the root of *Scutellaria baicalensis* Georgi, the stem of *Spatholobus suberectus* Dunn, the flower bud of *Syzygium aromaticum* (L.) Merr. et Perry, the bark of *Terminalia arjuna* Wight et A-rn., the fruit peel of *Terminalia belerica* Roxb., the fruit of *Terminalia chebula* Retzus, the flower and leaf of *Woodfordia floribunda* Salisb., the rhizome of *Woodwradia orientalis* Sw., and the fruit of *Zizyphus jujuba* Miller var. inermis Rehder.

4. A method for treating varicella-zoster viral infection, comprising orally administering to a subject in need thereof a therapeutically effective amount of an anti-varicella-zoster virus agent containing at least one crude drug selected from the group consisting of the rhizome of *Alpinia officinarum* Hance, the seed of *Areca catechu* L., the leaf of *Artemisia princeps* Pamp., the root of *Bupleurum fakatum* L., the bark of *Cassia fistula* L., the rhizome of *Coptis chinensis* Franch., the rhizome of *Cyrtomium fortunei* J. Sm., the rhizome of *Drynaria fortunei* (Kunze) J. Smith, the whole plant of *Geranium*

*thunbergii* Sieb. et Zucc., the root and stolon of *Glycyrrhiza uralensis* Fisher, the bark of *Juglans mandshurica* Maxim., the root bark of *Paeonia suffruticosa* Andrews, the root of *Panax ginseng* C. A. Meyer, the bark of *Phellodendron amurense* Ruprecht, the rhizome of *Plagiogyria matsumureana* Makino, the root of *Polygala tenuifolia* Willd., the root and rhizome of *Polygonum cuspidatum* Sieb. et Zucc., the hoelen of *Poria cocos* Wolf, the root bark and fruit peel of *Punica granatum* L., the bark of *Quercus acutissim* Carruthers, the rhizome of *Rheum palmatum* L., the gall of *Rhus javanica* L., the flower bud of *Syzygium aromaticum* (L.) Merr. et Perry, the bark of *Terminalia arjuna* Wight et Arn., the fruit of *Terminalia chebula* Retzus, the rhizome of *Woodwardia orientalis* Sw., and the rhizome of *Dryopteris crassirhizoma* Nakai.

5. A method for treating CMV infection, comprising orally administering to a subject in need thereof a therapeutically effective amount of an anti-CMV agent containing at least one crude drug selected from the group consisting of the seed of *Areca catechu* L., the leaf of *Artemisia princeps* Pamp., the bark of *Cassia fistula* L., the rhizome of *Coptis chinensis* Franch., the rhizome of *Cyrtomium fortunei* J. Sm., the rhizome of *Drynaria fortunei* (Kunze) J. Smith, the whole plant of *Geranium thunbergii* Sieb. et Zucc., the whole plant of *Geum japonicum* Thunb., the bark of *Juglans mandshurica* Maxim., the bark of *Machilus thunbergii* Sieb. et Zucc., the root bark of *Paeonia suffruticosa* Andrews, the bark of *Phellodendron amurense* Ruprecht, the rhizome of *Plagiogyria matsumureana* Makino, the root of *Polygala tenuifolia* Willd., the root and rhizome of *Polygonum cuspidatum* Sieb. et Zucc., the root bark and fruit peel of *Punica granatum* L., the bark of *Quercus acutissima* Carruthers, the rhizome of *Rheum palmatum* L., the gall of *Rhus javanica* L., the flower bud of *Syzgium aromaticum* (L.) Merr. et Perry, the bark of *Terminalia arjuna* Wight et Arn., the fruit of *Terminalia chebula* Retzus, and the rhizome of *Woodwardia orientalis* Sw.

* * * * *